United States Patent
Yoshizawa et al.

(10) Patent No.: US 12,239,908 B2
(45) Date of Patent: Mar. 4, 2025

(54) STORAGE MEDIUM HAVING STORED THEREON INFORMATION PROCESSING PROGRAM, AND INFORMATION PROCESSING DEVICE

(71) Applicants: Makoto Yoshizawa, Sendai (JP);
Tomoyuki Yambe, Sendai (JP);
Norihiro Sugita, Sendai (JP);
Norikatsu Furuta, Kyoto (JP)

(72) Inventors: Makoto Yoshizawa, Sendai (JP);
Tomoyuki Yambe, Sendai (JP);
Norihiro Sugita, Sendai (JP);
Norikatsu Furuta, Kyoto (JP)

(73) Assignees: NINTENDO CO., LTD., Kyoto (JP);
TOHOKU UNIVERSITY, Miyagi (JP)

( * ) Notice: Subject to any disclaimer, the term of this patent is extended or adjusted under 35 U.S.C. 154(b) by 1278 days.

(21) Appl. No.: 16/890,874

(22) Filed: Jun. 2, 2020

(65) Prior Publication Data
US 2020/0289927 A1 Sep. 17, 2020

Related U.S. Application Data

(63) Continuation of application No. 14/844,781, filed on Sep. 3, 2015, now Pat. No. 10,709,978, which is a (Continued)

(30) Foreign Application Priority Data

Mar. 26, 2009 (JP) ................................ 2009-076919

(51) Int. Cl.
*A63F 13/428* (2014.01)
*A61B 5/00* (2006.01)
(Continued)

(52) U.S. Cl.
CPC .......... *A63F 13/428* (2014.09); *A61B 5/0022* (2013.01); *A61B 5/0059* (2013.01);
(Continued)

(58) Field of Classification Search
CPC . A61B 5/0022; A61B 5/0205; A61B 5/02416; A61B 5/02438; A61B 5/1118;
(Continued)

(56) References Cited

U.S. PATENT DOCUMENTS 5,471,009 A 11/1995 Oba et al.
5,672,107 A 9/1997 Clayman
(Continued)

FOREIGN PATENT DOCUMENTS

JP 10-043430 2/1988
JP 2007-301048 11/2007

OTHER PUBLICATIONS

IGN "Tetris 64(Import)", Feb. 24, 1999.
(Continued)

*Primary Examiner* — Christian Jang
(74) *Attorney, Agent, or Firm* — Nixon & Vanderhye, P.C.

(57) ABSTRACT

An example computer readable storage medium having stored thereon an information processing program executable by a computer of an information processing device which presents information corresponding to a biological signal acquired from a user, is provided. The information processing program causes the computer to function as biological signal acquiring means, motion/attitude information acquiring means, and presentation means. The biological signal acquiring means acquires the biological signal from the user. The motion/attitude information acquiring means acquires information about a motion or an attitude of the user from detecting means, in association with the
(Continued)

biological signal acquired by the biological signal acquiring means. The presentation means performs predetermined presentation based on both the biological signal acquired by the biological signal acquiring means and the information acquired by the motion/attitude information acquiring means.

24 Claims, 18 Drawing Sheets

Related U.S. Application Data continuation of application No. 12/559,667, filed on Sep. 15, 2009, now Pat. No. 9,623,330.

(51) Int. Cl.
| | |
|---|---|
| *A61B 5/0205* | (2006.01) |
| *A61B 5/021* | (2006.01) |
| *A61B 5/024* | (2006.01) |
| *A61B 5/026* | (2006.01) |
| *A61B 5/08* | (2006.01) |
| *A61B 5/11* | (2006.01) |
| *A61B 5/1455* | (2006.01) |
| *A61B 5/24* | (2021.01) |
| *A61B 5/318* | (2021.01) |
| *A61B 5/389* | (2021.01) |
| *A61M 21/00* | (2006.01) |
| *A61M 21/02* | (2006.01) |
| *A63F 13/211* | (2014.01) |
| *A63F 13/212* | (2014.01) |

(52) U.S. Cl.
CPC .......... *A61B 5/0077* (2013.01); *A61B 5/0205* (2013.01); *A61B 5/02416* (2013.01); *A61B 5/02438* (2013.01); *A61B 5/0261* (2013.01); *A61B 5/1118* (2013.01); *A61B 5/24* (2021.01); *A61B 5/4035* (2013.01); *A61B 5/486* (2013.01); *A61B 5/6826* (2013.01); *A61B 5/6838* (2013.01); *A61B 5/6897* (2013.01); *A61B 5/7278* (2013.01); *A61B 5/744* (2013.01); *A61B 5/7455* (2013.01); *A61B 5/7475* (2013.01); *A61M 21/02* (2013.01); *A63F 13/211* (2014.09); *A63F 13/212* (2014.09); *A61B 5/021* (2013.01); *A61B 5/026* (2013.01); *A61B 5/0816* (2013.01); *A61B 5/14552* (2013.01); *A61B 5/318* (2021.01); *A61B 5/389* (2021.01); *A61B 2562/0219* (2013.01); *A61B 2562/222* (2013.01); *A61M 2021/0044* (2013.01); *A61M 2205/3561* (2013.01); *A61M 2205/3592* (2013.01); *A61M 2205/502* (2013.01); *A61M 2205/52* (2013.01); *A61M 2209/01* (2013.01); *A61M 2230/06* (2013.01); *A61M 2230/42* (2013.01); *A61M 2230/63* (2013.01); *A63F 2300/1012* (2013.01); *A63F 2300/105* (2013.01); *A63F 2300/6045* (2013.01)

(58) Field of Classification Search
CPC ................. A61B 5/6897; A61B 5/744; A61B 2562/0219
See application file for complete search history.

(56) References Cited

U.S. PATENT DOCUMENTS

| | | | |
|---|---|---|---|
| 7,012,182 | B2 | 3/2006 | Nishitani et al. |
| 7,331,870 | B2* | 2/2008 | Smith ................. A63F 13/30 463/40 |
| 9,327,190 | B2 | 5/2016 | Yoshizawa et al. |
| 9,623,330 | B2 | 4/2017 | Yoshizawa et al. |
| 2002/0065454 | A1 | 5/2002 | Lebel et al. |
| 2002/0109600 | A1 | 8/2002 | Mault et al. |
| 2003/0036417 | A1* | 2/2003 | Ueshima ............... A63F 13/812 463/4 |
| 2006/0022833 | A1 | 2/2006 | Ferguson et al. |
| 2006/0047202 | A1 | 3/2006 | Elliott |
| 2006/0075816 | A1 | 4/2006 | Bremer et al. |
| 2007/0021209 | A1 | 1/2007 | Hussaini et al. |
| 2007/0049374 | A1* | 3/2007 | Ikeda ................. A63F 13/42 463/30 |
| 2008/0139955 | A1 | 6/2008 | Hansmann et al. |
| 2008/0319252 | A1* | 12/2008 | Chapman ............ A63F 13/428 600/27 |
| 2010/0249494 | A1 | 9/2010 | Yoshizawa et al. |
| 2013/0231186 | A1 | 9/2013 | Yoshizawa et al. |

OTHER PUBLICATIONS

El Greco "Tetrist FAQ/Strategy Guide", Nov. 16, 2003.
Hasegawa et al., "The Relaxation Biofeedback System with Computer and Heart Rate Variability Interaction", The Institute of Electronics, Information and Communication Engineers, vol. 103, No. 470, Nov. 20, 2003, pp. 35-38.
Japanese Office Action dated Mar. 24, 2011 in Japanese Application No. 2009-076919.
Notice of Allowance and Fee(s) Due and Notice of Allowability dated Nov. 10, 2015 U.S. Appl. No. 13/861,599.
Office Action dated Jan. 27, 2014 in U.S. Appl. No. 13/861,599.
Yoshizawa et al., U.S. Appl. No. 14/844,781, filed Sep. 3, 2015.
Yoshizawa et al., U.S. Appl. No. 13/861,599, filed Apr. 12, 2013, now U.S. Pat. No. 9,327,190.
Yoshizawa et al., U.S. Appl. No. 12/559,667, filed Sep. 15, 2009, now U.S. Pat. No. 9,623,330.

* cited by examiner

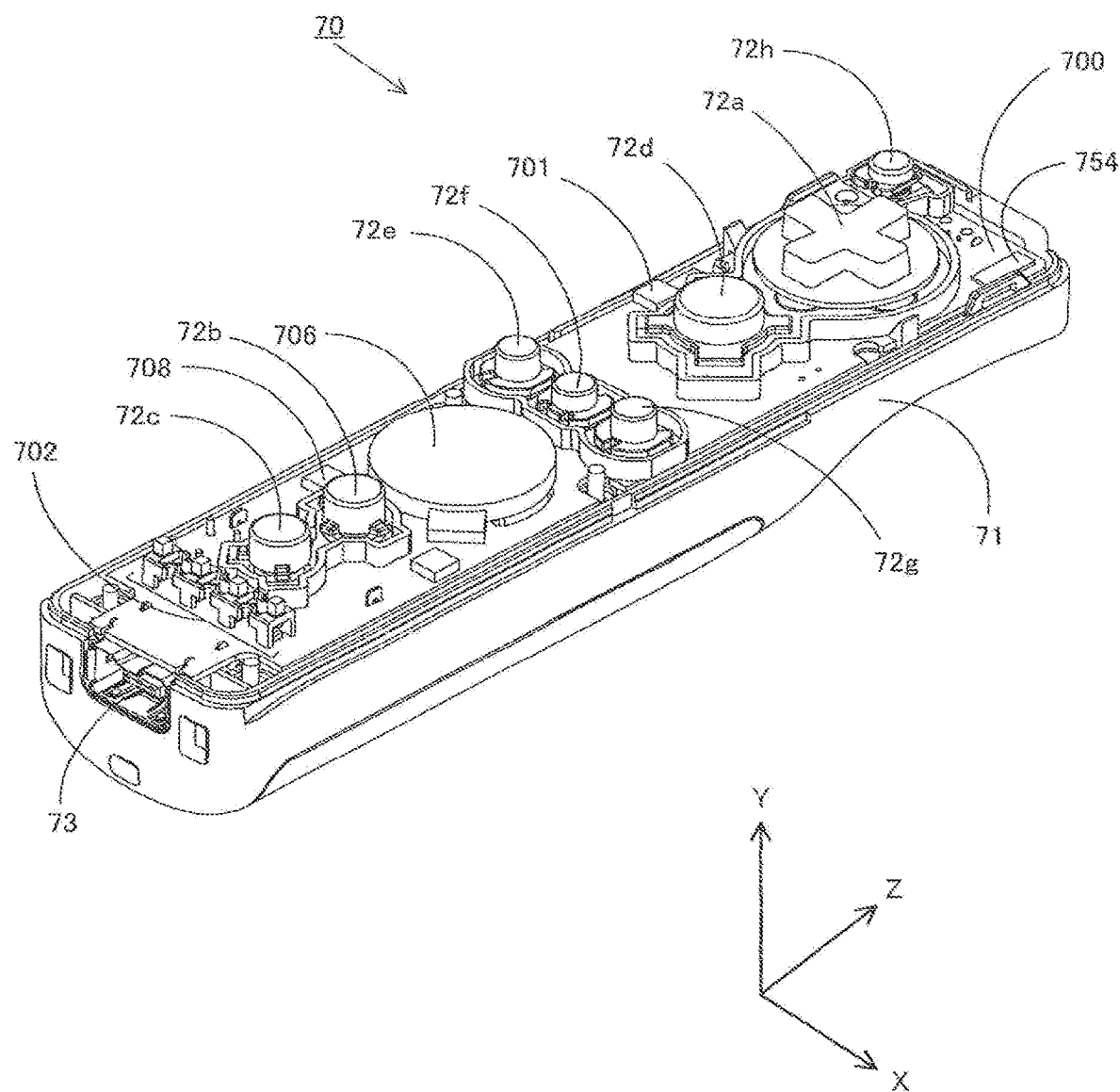
F I G. 5

STORAGE MEDIUM HAVING STORED THEREON INFORMATION PROCESSING PROGRAM, AND INFORMATION PROCESSING DEVICE

CROSS REFERENCE TO RELATED APPLICATION

This application is a continuation of U.S. patent application Ser. No. 14/844,781, filed on Sep. 3, 2015, now U.S. Pat. No. 10,709,978, which is a continuation of U.S. patent application Ser. No. 12/559,667, filed Sep. 15, 2009, now U.S. Pat. No. 9,623,330, which claims priority to Japanese Patent Application No. 2009-076919, filed Mar. 26, 2009. The entire contents of each of these applications are hereby incorporated by reference herein.

BACKGROUND

Technical Field

The present invention relates to a storage medium having stored thereon an information processing program and an information processing device. More particularly, the present invention relates to a storage medium having stored thereon an information processing program and an information processing device which perform predetermined presentation based on a biological signal of the user.

Description of Background Art

For example, Takayuki HASEGAWA and Kiyoko YOKOYAMA, "The Relaxation Biofeedback System With Computer and Heart Rate Variability Interaction", IEICE technical report, ME and bio cybernetics, The Institute of Electronics, Information and Communication Engineers, Vol. 103, No. 470, pp. 35-38, Nov. 20, 2003 (hereinafter referred to as Non-Patent Document 1) proposes a biofeedback system for stress management or relaxation treatment. The system estimates and presents a relaxation level in real time based on measured heart rate information of the user. Moreover, the system interacts with the user to improve a relaxation effect on the user, thereby providing a function of performing biofeedback in a manner adapted for the individual user.

In the biofeedback system described in Non-Patent Document 1, a value (called a relaxation level) calculated based on the heart rate information or the like of the user, is represented by or reflected on a motion of a character or an environment in a sandtray. The biofeedback system thereby interacts with the user in a manner which improves the relaxation effect. However, this representation only visually presents the relaxation level to the user, so that the user can only recognize a current relaxation level.

SUMMARY

Therefore, an object of the present invention is to provide a storage medium having stored thereon an information processing program and an information processing device which perform predetermined presentation using a current biological signal of the user and a current motion or attitude of the user, thereby prompting the user to change their state.

The present invention has the following features to attain the object mentioned above. Note that reference numerals, additional descriptions and the like inside parentheses in this section indicate correspondence to embodiments described below for the sake of easy understanding, and do not limit the present invention.

A first aspect of the present invention is directed to a computer readable storage medium having stored thereon an information processing program executable by a computer (10) of an information processing device (5) which presents information corresponding to a biological signal (Dc) acquired from a user. The information processing program causes the computer to function as biological signal acquiring means (a CPU 10 executing steps 42, 49, 82 and 84; hereinafter only step numbers are described), motion/attitude information acquiring means (S84), and presentation means (S44, S46, S51, S52, S86, S90, S92, S104, S107 and S111). The biological signal acquiring means acquires the biological signal from the user. The motion/attitude information acquiring means acquires information about a motion or an attitude of the user from detecting means (701), in association with the biological signal acquired by the biological signal acquiring means. The presentation means performs predetermined presentation based on both the biological signal acquired by the biological signal acquiring means and the information acquired by the motion/attitude information acquiring means.

In a second aspect based on the first aspect, the information processing program causes the computer to further function as motion determining means (S85). The motion determining means determines a motion of an input device (70) operated by the user, based on the information acquired by the motion/attitude information acquiring means. The presentation means performs the presentation based on both the biological signal acquired by the biological signal acquiring means and the motion of the input device determined by the motion determining means.

In a third aspect based on the first aspect, the information processing program causes the computer to further function as instruction means. The instruction means instructs the user to take a predetermined motion or attitude.

In a fourth aspect based on the third aspect, the presentation means performs the presentation based on both the biological signal and the information acquired by the motion/attitude information acquiring means, the biological signal and the information being acquired when the instruction means performs instruction.

In a fifth aspect based on the third aspect, the information processing program causes the computer to further function as determination means. The determination means determines whether or not the user is in the motion or attitude which the instruction means instructs the user to take, based on the information acquired by the motion/attitude information acquiring means. The presentation means performs the presentation based on the biological signal acquired by the biological signal acquiring means, during or after the determination means determines that the user is in the motion or attitude which the instruction means instructs the user to take.

In a sixth aspect based on the third aspect, the instruction means instructs the user to take a motion or an attitude which causes a predetermined biological signal to be output.

In a seventh aspect based on the second aspect, the presentation means performs presentation (a ceiling T and a ground B) indicating an operation moving the input device corresponding to a motion of the input device which can be determined by the motion determining means.

In an eighth aspect based on the first aspect, the presentation means performs presentation indicating a predetermined motion or attitude of the user, based on both the biological signal acquired by the biological signal acquiring means and the information acquired by the motion/attitude information acquiring means.

In a ninth aspect based on the eighth aspect, the presentation means performs presentation indicating a motion or an attitude causing a change in the biological signal, based on the biological signal acquired by the biological signal acquiring means.

In a tenth aspect based on the first aspect, the biological signal acquiring means acquires as the biological signal a signal relating to pulsation or heartbeat of the user.

In an eleventh aspect based on the first aspect, the biological signal acquiring means acquires as the biological signal at least one selected from the group consisting of a pulse wave, a heart rate, an activity level of the sympathetic nervous system, an activity level of the parasympathetic nervous system, a heart rate variance coefficient, a cardiac cycle, a respiration frequency, and a pulse wave amplitude of the user.

In a twelfth aspect based on the eleventh aspect, the biological signal acquiring means acquires at least the pulse wave amplitude of the user. The presentation means determines a difficulty level of the user using a change in the pulse wave amplitude of the user, and performs presentation indicating a motion based on a result of the determination.

In a thirteenth aspect based on the second aspect, the input device includes an acceleration sensor (701). The motion determining means determines a motion of the input device using an acceleration indicated by acceleration data (Da) outputted from the acceleration sensor.

In a fourteenth aspect based on the thirteenth aspect, the motion determining means determines a motion of the input device based on an inclination of the input device with reference to a direction of gravity, where the direction of gravity is the acceleration indicated by the acceleration data outputted from the acceleration sensor.

In a fifteenth aspect based on the second aspect, the input device includes a gyro-sensor. The motion determining means determines a motion of the input device using an angular velocity indicated by angular velocity data outputted from the gyro-sensor.

In a sixteenth aspect based on the first aspect, the presentation means performs the presentation by displaying on a display device (2) at least either of an image and characters generated based on both the biological signal acquired by the biological signal acquiring means and the information acquired by the motion/attitude information acquiring means.

In a seventeenth aspect based on the sixteenth aspect, the presentation means performs the presentation by displaying on the display device an object (PC) generated based on both the biological signal acquired by the biological signal acquiring means and the information acquired by the motion/attitude information acquiring means.

In an eighteenth aspect based on the first aspect, the presentation means performs the presentation by controlling a motion of a predetermined object displayed on a display device, based on both the biological signal acquired by the biological signal acquiring means and the information acquired by the motion/attitude information acquiring means.

In a nineteenth aspect based on the eighteenth aspect, the presentation means performs presentation in which the object performs a first motion in a virtual world based on the biological signal acquired by the biological signal acquiring means, and performs presentation in which the object performs a second motion different from the first motion in the virtual world based on the information acquired by the motion/attitude information acquiring means.

In a twentieth aspect based on the nineteenth aspect, the presentation means moves at least a portion of the object in the virtual world as one of the first and second motions, and changes an attitude of the object in the virtual world as the other of the first and second motions.

In a twenty-first aspect based on the twelfth aspect, the presentation means moves at least a portion of the object in a predetermined first direction in the virtual world as one of the first and second motions, and moves at least a portion of the object in a predetermined second direction in the virtual world as the other of the first and second motions.

In a twenty-second aspect based on the eighteenth aspect, the information processing program causes the computer to further function as object motion determining means. The object motion determining means determines a motion of the object in the virtual world.

In a twenty-third aspect based on the twenty-second aspect, the information processing program causes the computer to further function as instruction means. The instruction means instructs the user to take a predetermined motion or attitude by causing a topographical object for designating a motion of the object to appear in the virtual world. The object motion determining means determines whether or not the object contacts the topographical object.

In a twenty-fourth aspect based on the twenty-third aspect, the instruction means changes the topographical object, depending on the biological signal acquired by the biological signal acquiring means.

In a twenty-fifth aspect based on the nineteenth aspect, the presentation means moves at least a portion of the object in a predetermined direction as the first motion, depending on a biological signal relating to respiration of the user acquired by the biological signal acquiring means.

In a twenty-sixth aspect based on the twenty-fifth aspect, the presentation means performs the presentation by further displaying on the display device an obstacle (ceiling T) in the virtual world which limits a movement in the predetermined direction of the object, the objects rising and falling based a respiration frequency of the user acquired from the biological signal acquired by the biological signal acquiring means. The information processing program causes the computer to further function as assessment means (S101 and S102). The assessment means degrades assessment when the object contacts or overlaps the rising and falling obstacle in the virtual world.

In a twenty-seventh aspect based on the nineteenth aspect, the biological signal acquiring means acquires at least a pulse wave amplitude of the user. The presentation means performs the presentation by determining a difficulty level of the user using a change in the pulse wave amplitude of the user acquired by the biological signal acquiring means, and when determining the user has difficulty, changing a way in which the object is displayed.

In a twenty-eighth aspect based on the twenty-seventh aspect, the presentation means changes and inclines an attitude of the object in the virtual world as the second motion based on the information acquired by the motion/attitude information acquiring means. The information processing program causes the computer to further function as assessment means. The assessment means degrades assessment when the object contacts or overlaps an obstacle (ground B) in the virtual world, an inclination angle of the obstacle limiting an inclining motion of the object in the virtual world. The assessment means gradually increases and changes the inclination angle of the obstacle with time, and when the presentation means determines that the user has difficulty, stops changing the inclination angle of the obstacle.

In a twenty-ninth aspect based on the first aspect, the presentation means performs the presentation by outputting audio based on both the biological signal acquired by the biological signal acquiring means and the information acquired by the motion/attitude information acquiring means.

A thirtieth aspect is directed to an information processing device for presenting information corresponding to a biological signal acquired from a user. The information processing device includes biological signal acquiring means, motion/attitude information acquiring means, and presentation means. The biological signal acquiring means acquires the biological signal from the user. The motion/attitude information acquiring means acquires information about a motion or an attitude of the user from detecting means, in association with the biological signal acquired by the biological signal acquiring means. The presentation means performs predetermined presentation based on both the biological signal acquired by the biological signal acquiring means and the information acquired by the motion/attitude information acquiring means.

According to the first aspect, predetermined presentation is performed using not only a current user's biological signal, but also a current user's motion or attitude. Therefore, the user can recognize a state of their body to larger extent, and a change in a state of the user's body can be promoted by combination of a user's motion or attitude.

According to the second aspect, a current user's motion or attitude can be detected by the user moving the input device.

According to the third aspect, the user can be caused to take an appropriate motion or attitude.

According to the fourth aspect, presentation can be performed based on information which is obtained when the user takes an instructed motion or attitude.

According to the fifth aspect, a change in biological signal caused by the user taking an instructed motion or attitude can be presented.

According to the sixth aspect, it is possible to instruct the user to take a motion or an attitude which generates an appropriate biological signal.

According to the seventh aspect, the user is prompted to move the input device, and therefore, a change in a state of the user's body can be promoted by the user's act of moving the input device.

According to the eighth aspect, the user is prompted to take a motion or an attitude based on a user's biological signal. Therefore, a change in a state of the user's body relating to the biological signal can be promoted by the user's motion or attitude.

According to the ninth aspect, the user can be prompted to take a motion or an attitude which causes a change in a user's biological signal.

According to the tenth aspect, presentation relating to a user's pulse rate or heart rate can be performed.

According to the eleventh aspect, presentation can be performed for the user using a pulse wave, a heart rate, an activity level of the sympathetic nervous system, an activity level of the parasympathetic nervous system, a heart rate variance coefficient, a cardiac cycle, a respiration frequency, or a pulse wave amplitude.

According to the twelfth aspect, a difficulty level of the user is determined. Therefore, it is possible to instruct the user to take an appropriate motion or attitude based on a result of the determination.

According to the thirteenth aspect, a motion of the input device can be determined based on an acceleration acting on the input device.

According to the fourteenth aspect, an inclination of the input device can be determined with reference to a direction of gravity acting on the input device.

According to the fifteenth aspect, a motion of the input device can be determined using rotation of the input device.

According to the sixteenth aspect, an image or characters are presented based on a user's biological signal and a user's motion or attitude. Therefore, the user can recognize a state of their body to larger extent, and a change in a state of the user's body can be promoted by combination of a user's motion or attitude.

According to the seventeenth and eighteenth aspects, an object is presented based on a user's biological signal and a user's motion or attitude in the virtual world. Therefore, the user can recognize a state of their body to larger extent, and a change in a state of the user's body can be promoted by combination of a user's motion or attitude.

According to the nineteenth aspect, an object in the virtual world performs different motions based on a user's biological signal and a user's motion or attitude. Therefore, the user can recognize and distinguish presentation based on their biological signal from presentation based on their motion or attitude. As a result, the user can move an object based on their biological signal while moving the object based on their motion or attitude.

According to the twentieth aspect, an object in the virtual space can be inclined and a portion of the object is moved based on a user's motion or attitude and a user's biological signal.

According to the twenty-first aspect, an object in the virtual world is moved in different directions based on a user's biological signal and a user's motion or attitude. Therefore, the user can recognize and distinguish presentation based on their biological signal from presentation based on their motion or attitude. As a result, the user can move an object based on their biological signal while moving the object based on their motion or attitude.

According to the twenty-second aspect, a motion of an object can be used to assess a user's biological signal or a user's motion or attitude.

According to the twenty-third aspect, an operation depending on a topographical object is required. Therefore, a state of the user's body can be promoted by causing the user to generate a biological signal corresponding to the operation, perform a motion corresponding to the operation, or take an attitude corresponding to the operation.

According to the twenty-fourth aspect, it is possible to instruct the user to perform an appropriate operation based on a user's biological signal.

According to the twenty-fifth aspect, a portion of an object can be moved in a predetermined direction based on user's respiration.

According to the twenty-sixth aspect, the user has to operate an object in a manner which allows the object to avoid an obstacle, and therefore, has to breathe in a manner which allows the object to avoid the obstacle. On the other hand, a shape of the obstacle is determined based on a user's respiration frequency. Therefore, it is possible to provide a shape of the object which can gradually decrease the user's respiration frequency. It is also possible to provide a shape of the object which can gradually increase the user's respiration frequency.

According to the twenty-seventh aspect, a difficulty level of the user can be presented by a way in which an object is displayed.

According to the twenty-eighth aspect, the user has to operate an object in a manner which allows the object to avoid an obstacle, and therefore, has to take a motion or attitude which allows the object to avoid the obstacle. When the user performs a motion corresponding to an inclination of the obstacle, then if the user has difficulty in doing so, the inclination of the obstacle is no longer changed. Therefore, control can be performed, depending on the difficulty level of the user.

According to the twenty-ninth aspect, audio is presented based on a user's biological signal and a user's motion or attitude. Therefore, the user can recognize a state of their body to larger extent, and a change in a state of the user's body can be promoted by combination of a user's motion or attitude.

According to the information processing device of the present invention, effects similar to those of the aforementioned storage medium having stored thereon the information processing program can be obtained.

These and other objects, features, aspects and advantages of the present invention will become more apparent from the following detailed description of the present invention when taken in conjunction with the accompanying drawings.

BRIEF DESCRIPTION OF THE DRAWINGS

FIG. 5 is an isometric view, showing that an upper casing of the core unit 70 of FIG. 3 is removed;

DETAILED DESCRIPTION OF EXAMPLE EMBODIMENTS

Figure 1:
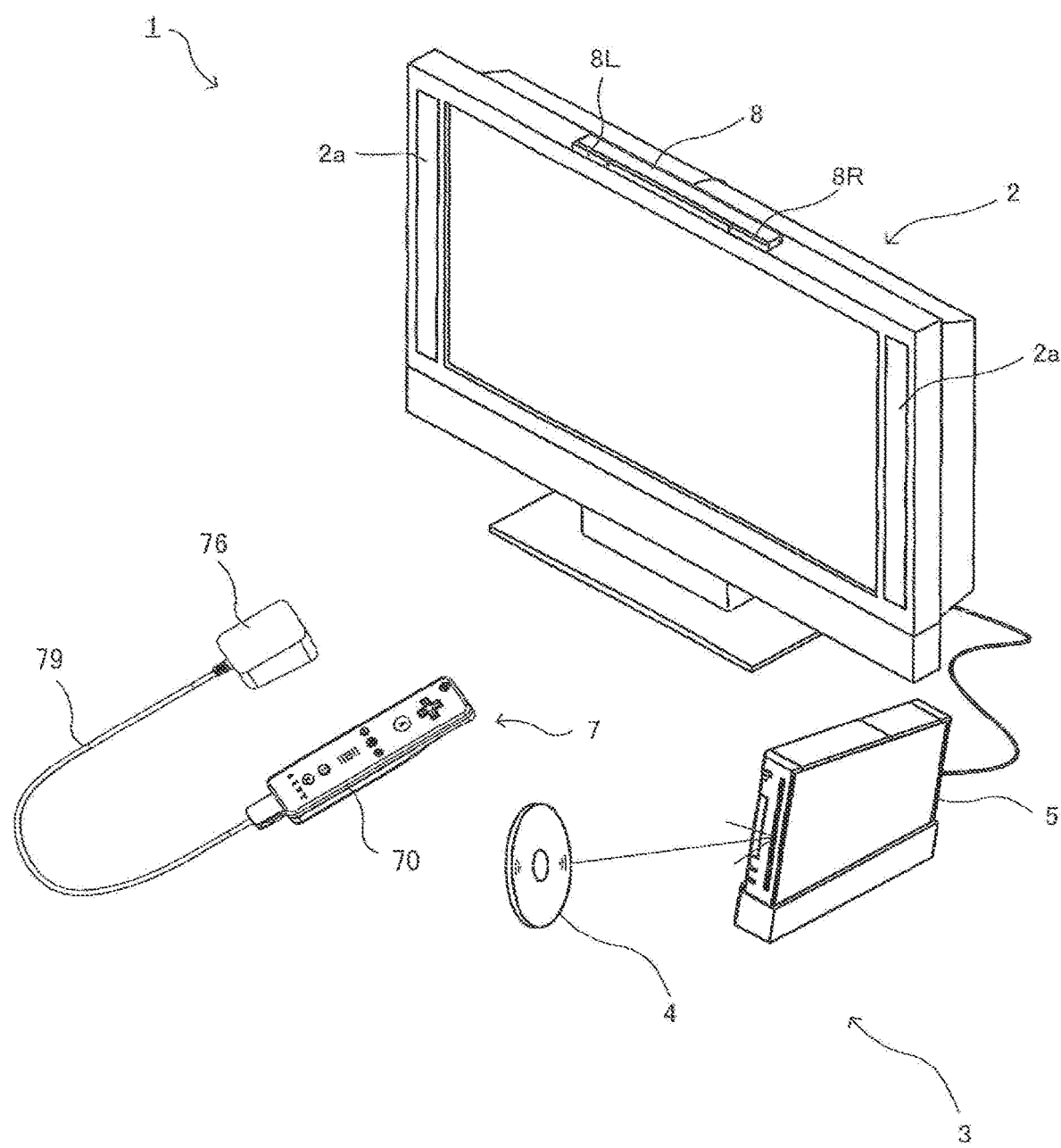
FIG. 1 is an external view showing an example of a game system 1 according to an embodiment of the present invention.
Figure 2:
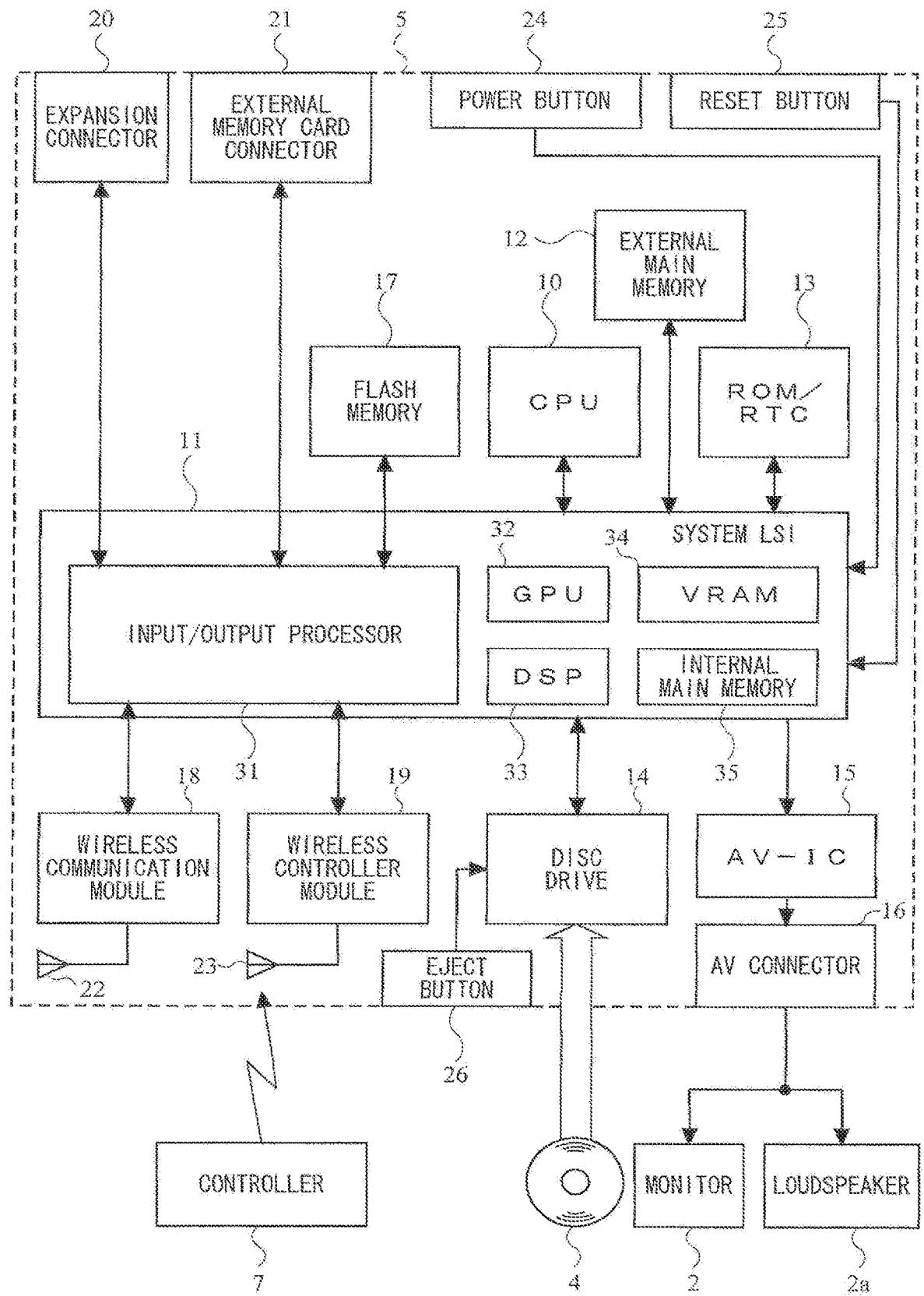
FIG. 2 is a block diagram showing an example of a game apparatus body 5 of FIG. 1.

With reference to FIG. 1, an apparatus for executing an information processing program according to an embodiment of the present invention, will be described. Hereinafter, in order to give a specific description, a description will be given using a game system including a stationary game apparatus body 5 that is an example of the above apparatus. FIG. 1 is an external view showing an example of a game system 1 including a stationary game apparatus 3. FIG. 2 is a block diagram showing an example of the game apparatus body 5. The game system 1 will be described below.

As shown in FIG. 1, the game system 1 includes: a home-use TV receiver 2 (hereinafter, referred to as a monitor 2) which is an example of display means; and the stationary game apparatus 3 connected to the monitor 2 via a connection cord. The monitor 2 has loudspeakers 2a for outputting, in the form of sound, an audio signal outputted from the game apparatus 3. The game apparatus 3 includes: an optical disc 4 storing a game program that is an example of an information processing program of the present invention; the game apparatus body 5 having a computer for executing the game program of the optical disc 4 to cause the monitor 2 to output and display a game screen; and a controller 7 for providing the game apparatus body 5 with necessary operation information for a game in which a character or the like displayed in the game screen is controlled.

The game apparatus body 5 has a wireless controller module 19 therein (see FIG. 2). The wireless controller module 19 receives data wirelessly transmitted from the controller 7, and transmits data from the game apparatus body 5 to the controller 7. In this manner, the controller 7 and the game apparatus body 5 are connected by wireless communication. Further, the optical disc 4 as an example of an exchangeable information storage medium is detachably mounted on the game apparatus body 5.

On the game apparatus body 5, a flash memory 17 (see FIG. 2) is mounted, the flash memory 17 acting as a backup memory for fixedly storing such data as saved data. The game apparatus body 5 executes the game program or the like stored on the optical disc 4, and displays a result thereof as a game image on the monitor 2. The game program or the like to be executed may be prestored not only on the optical disc 4, but also in the flash memory 17. The game apparatus body 5 can reproduce a state of the game played in the past, by using the saved data stored in the flash memory 17, and display a game image of the reproduced state on the monitor 2. A user of the game apparatus 3 can enjoy advancing in the game by operating the controller 7 while watching the game image displayed on the monitor 2.

By using the technology of, for example, Bluetooth (registered trademark), the controller 7 wirelessly transmits transmission data, such as operation information and biological information, to the game apparatus body 5 having the wireless controller module 19 therein. The controller 7 includes a core unit 70 and a vital sensor 76. The core unit 70 and the vital sensor 76 are connected to each other via a flexible connection cable 79. The core unit 70 is operation means mainly for controlling an object or the like displayed on a display screen of the monitor 2. The vital sensor 76 is attached to a user's body (e.g., to the user's finger). The vital sensor obtains biological signals from the user, and sends biological information to the core unit 70 via the connection cable 79. The core unit 70 includes a housing, which is small enough to be held by one hand, and a plurality of operation buttons (including a cross key, a stick or the like) exposed at a surface of the housing. As described later in detail, the core unit 70 includes an imaging information calculation section 74 for taking an image of a view seen from the core unit 70. As an example of imaging targets of the imaging information calculation section 74, two LED modules 8L and 8R (hereinafter, referred to as "markers 8L and 8R") are provided in the vicinity of the display screen of the monitor 2. These markers 8L and 8R each output, for example, an infrared light forward from the monitor 2. The controller 7 (e.g., the core unit 70) is capable of receiving, via a communication section 75, transmission data wirelessly transmitted from the wireless controller module 19 of the game apparatus body 5, and generating a sound or vibration based on the transmission data.

Note that, in this example, the core unit 70 and the vital sensor 76 are connected by the flexible connection cable 79. However, the connection cable 79 can be eliminated by mounting a wireless unit on the vital sensor 76. For example, by mounting a Bluetooth (registered trademark) unit on the vital sensor 76 as a wireless unit, transmission of biological information from the vital sensor 76 to the core unit 70 or to the game apparatus body 5 is enabled. Further, the core unit and the vital sensor 76 may be integrated, by fixedly providing the vital sensor 76 on the core unit 70. In this case, a user can use the vital sensor 76 integrated with the core unit 70.

Next, an internal configuration of the game apparatus body 5 will be described with reference to FIG. 2. FIG. 2 is a block diagram showing the internal configuration of the game apparatus body 5. The game apparatus body 5 has a CPU (Central Processing Unit) 10, a system LSI (Large Scale Integration) 11, an external main memory 12, a ROM/RTC (Read Only Memory/Real Time Clock) 13, a disc drive 14, an AV-IC (Audio Video-Integrated Circuit) 15, and the like.

The CPU 10 performs game processing by executing the game program stored in the optical disc 4, and acts as a game processor. The CPU 10 is connected to the system LSI 11. In addition to the CPU 10, the external main memory 12, the ROM/RTC 13, the disc drive 14 and the AV-IC 15 are connected to the system LSI 11. The system LSI 11 performs processing such as: controlling data transfer among components connected to the system LSI 11; generating an image to be displayed; obtaining data from external devices; and the like. An internal configuration of the system LSI 11 will be described later. The external main memory 12 that is a volatile memory stores a program, for example, a game program loaded from the optical disc 4, or a game program loaded from the flash memory 17, and also stores various data. The external main memory 12 is used as a work area or buffer area of the CPU 10. The ROM/RTC 13 has a ROM in which a boot program for the game apparatus body 5 is incorporated (a so-called a boot ROM), and has a clock circuit (RTC) which counts the time. The disc drive 14 reads program data, texture data and the like from the optical disc 4, and writes the read data into a later-described internal main memory 35 or into the external main memory 12.

On the system LSI 11, an input/output processor 31, a GPU (Graphic Processor Unit) 32, a DSP (Digital Signal Processor) 33, a VRAM (Video RAM) 34, and the internal main memory 35 are provided. Although not shown, these components 31 to 35 are connected to each other via an internal bus.

The GPU 32 is a part of rendering means, and generates an image in accordance with a graphics command from the CPU 10. The VRAM 34 stores necessary data for the GPU 32 to execute the graphics command (data such as polygon data, texture data and the like). At the time of generating the image, the GPU 32 uses the data stored in the VRAM 34, thereby generating image data.

The DSP 33 acts as an audio processor, and generates audio data by using sound data and sound waveform (tone) data stored in the internal main memory 35 and in the external main memory 12.

The image data and the audio data generated in the above manner are read by the AV-IC 15. The AV-IC 15 outputs the read image data to the monitor 2 via the AV connector 16, and outputs the read audio data to the loudspeakers 2a embedded in the monitor 2. As a result, an image is displayed on the monitor 2 and a sound is outputted from the loudspeakers 2a.

The input/output processor (I/O Processor) 31 performs, for example, data transmission/reception to/from components connected thereto, and data downloading from external devices. The input/output processor 31 is connected to the flash memory 17, a wireless communication module 18, the wireless controller module 19, an expansion connector 20, and an external memory card connector 21. An antenna 22 is connected to the wireless communication module 18, and an antenna 23 is connected to the wireless controller module 19.

The input/output processor 31 is connected to a network via the wireless communication module 18 and the antenna 22 so as to be able to communicate with other game apparatuses and various servers connected to the network. The input/output processor 31 regularly accesses the flash memory 17 to detect presence or absence of data that is required to be transmitted to the network. If such data is present, the data is transmitted to the network via the wireless communication module 18 and the antenna 22. Also, the input/output processor 31 receives, via the network, the antenna 22 and the wireless communication module 18, data transmitted from other game apparatuses or data downloaded from a download server, and stores the received data in the flash memory 17. By executing the game program, the CPU 10 reads the data stored in the flash memory 17, and the game program uses the read data. In addition to the data transmitted and received between the game apparatus body 5 and other game apparatuses or various servers, the flash memory 17 may store saved data of a game that is played using the game apparatus body 5 (such as result data or progress data of the game).

Further, the input/output processor 31 receives, via the antenna 23 and the wireless controller module 19, operation data or the like transmitted from the controller 7, and stores (temporarily) the operation data or the like in a buffer area of the internal main memory 35 or of the external main memory 12. Note that, similarly to the external main memory 12, the internal main memory 35 may store a program, for example, a game program loaded from the optical disc 4 or a game program loaded from the flash memory 17, and also store various data. The internal main memory 35 may be used as a work area or buffer area of the CPU 10.

In addition, the expansion connector 20 and the external memory card connector 21 are connected to the input/output processor 31. The expansion connector 20 is a connector for such interface as USB, SCSI or the like. The expansion connector 20, instead of the wireless communication module 18, is able to perform communication with a network by being connected to such a medium as an external storage medium, to such a peripheral device as another controller, or to a connector for wired communication. The external memory card connector 21 is a connector to be connected to an external storage medium such as a memory card. For example, the input/output processor 31 is able to access the external storage medium via the expansion connector 20 or the external memory card connector 21 to store or read data from the external storage medium.

On the game apparatus body 5 (e.g., on a front main surface thereof), a power button 24 of the game apparatus body 5, a reset button 25 for resetting game processing, an insertion slot for mounting the optical disc 4 in a detachable manner, an eject button 26 for ejecting the optical disc 4 from the insertion slot of the game apparatus body 5, and the like are provided. The power button 24 and the reset button 25 are connected to the system LSI 11. When the power button 24 is turned on, each component of the game apparatus body 5 is supplied with power via an AC adaptor that is not shown. When the reset button 25 is pressed, the system LSI 11 re-executes the boot program of the game apparatus body 5. The eject button 26 is connected to the disc drive 14. When the eject button 26 is pressed, the optical disc 4 is ejected from the disc drive 14.

Figure 3:
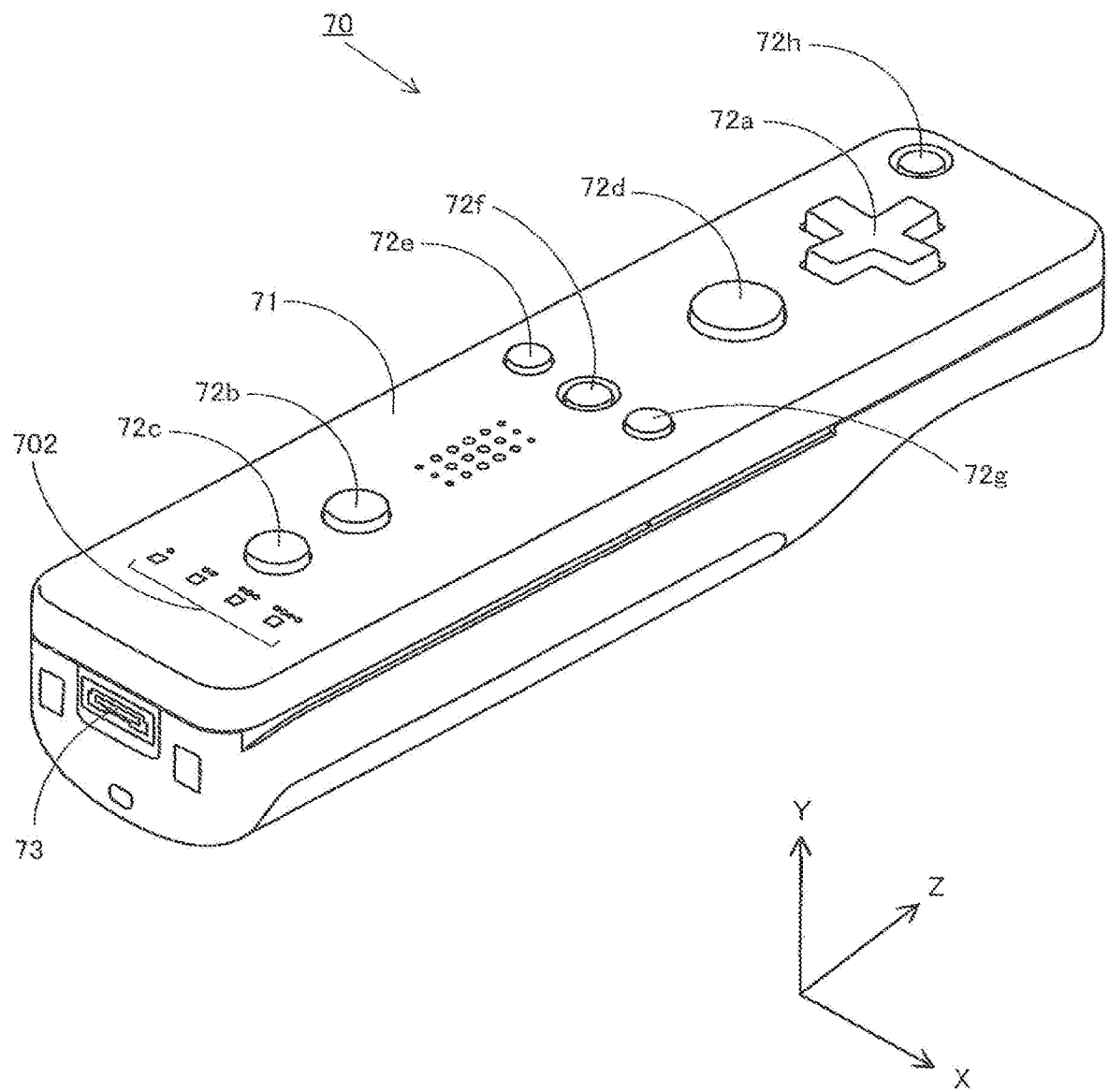
FIG. 3 is an isometric view of a core unit 70 of FIG. 1 seen from a top rear side thereof.
Figure 4:
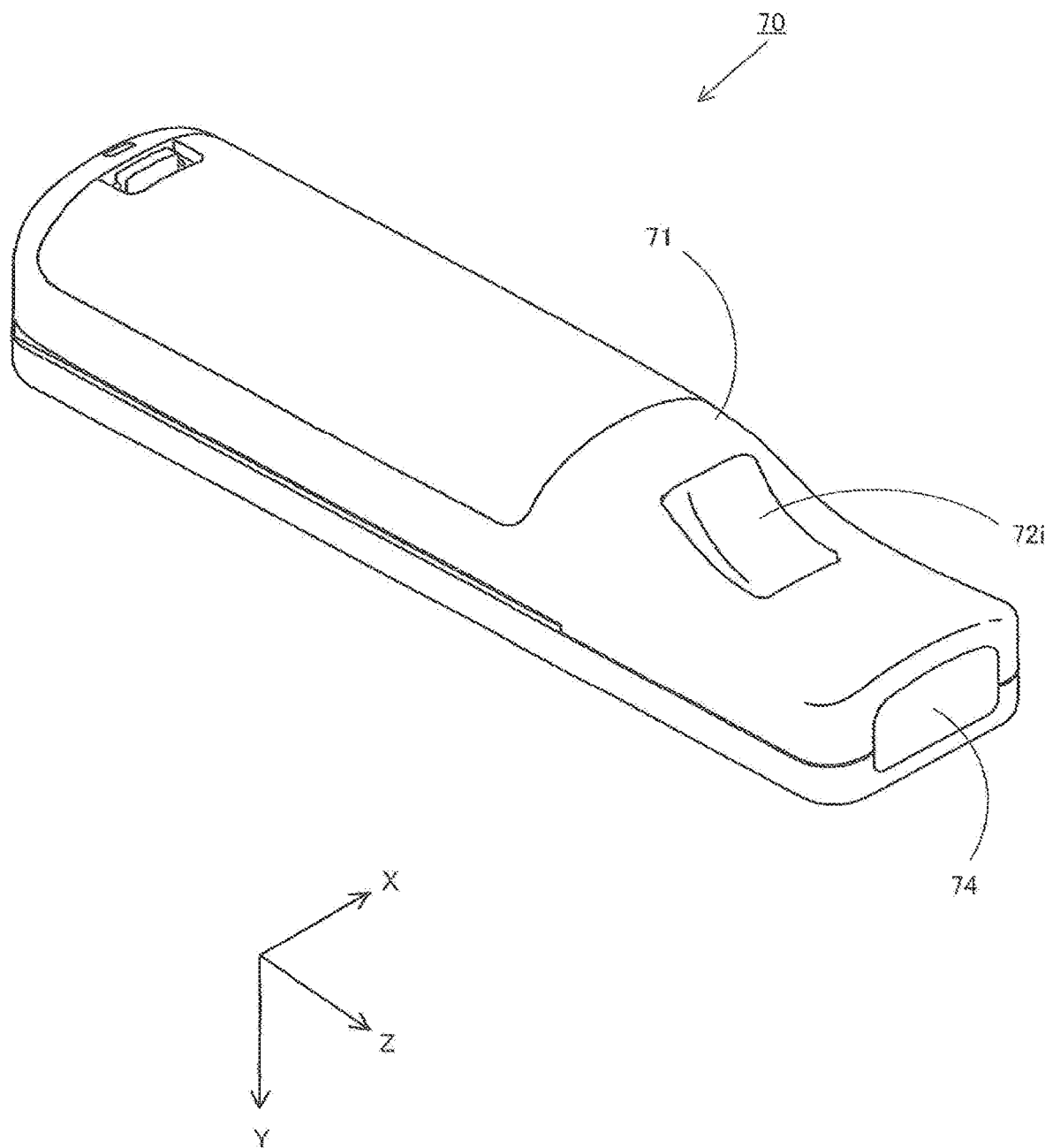
FIG. 4 is an isometric view of the core unit 70 of FIG. 3 seen from a bottom front side thereof.

With reference to FIGS. 3 and 4, the core unit 70 will be described. FIG. 3 is an isometric view of the core unit 70 seen from a top rear side thereof. FIG. 4 is an isometric view of the core unit 70 seen from a bottom front side thereof.

As shown in FIGS. 3 and 4, the core unit 70 includes a housing 71 formed by plastic molding or the like. The housing 71 has a plurality of operation sections 72 provided thereon. The housing 71 has an approximately parallelepiped shape extending in a longitudinal direction from front to rear. The overall size of the housing 71 is small enough to be held by one hand of an adult or even a child.

At the center of a front part of a top surface of the housing 71, a cross key 72a is provided. The cross key 72a is a cross-shaped four-direction push switch. The cross key 72a includes operation portions corresponding to four directions (front, rear, right and left), which are respectively located on cross-shaped projecting portions arranged at intervals of 90 degrees. A user selects one of the front, rear, right and left directions by pressing one of the operation portions of the cross key 72a. Through an operation of the cross key 72a, the user can, for example, designate a direction in which a player character or the like appearing in a virtual game world is to move, or give an instruction to select one of a plurality of options.

The cross key 72a is an operation section for outputting an operation signal in accordance with the aforementioned direction input operation performed by the user. Such an operation section may be provided in a different form. For example, an operation section, which has four push switches arranged in a cross formation and which is capable of outputting an operation signal in accordance with pressing of one of the push switches by the user, may be provided. Alternatively, an operation section, which has a composite switch having, in addition to the above four push switches, a center switch provided at an intersection point of the above cross formation, may be provided. Still alternatively, the cross key 72a may be replaced with an operation section which includes an inclinable stick (so-called a joy stick) projecting from the top surface of the housing 71 and which outputs an operation signal in accordance with an inclining direction of the stick. Still alternatively, the cross key 72a may be replaced with an operation section which includes a horizontally-slidable disc-shaped member and which outputs an operation signal in accordance with a sliding direction of the disc-shaped member. Still alternatively, the cross key 72a may be replaced with a touch pad.

Behind the cross key 72a on the top surface of the housing 71, a plurality of operation buttons 72b to 72g are provided. The operation buttons 72b to 72g are each an operation section for, when the user presses a head thereof, outputting a corresponding operation signal. For example, functions as a 1st button, a 2nd button and an A button are assigned to the operation buttons 72b to 72d. Also, functions as a minus button, a home button and a plus button are assigned to the operation buttons 72e to 72g, for example. Operation functions are assigned to the respective operation buttons 72a to 72g in accordance with the game program executed by the game apparatus body 5. In the exemplary arrangement shown in FIG. 3, the operation buttons 72b to 72d are arranged in a line at the center on the top surface of the housing 71 in a front-rear direction. The operation buttons 72e to 72g are arranged on the top surface of the housing 71 in a line in a left-right direction between the operation buttons 72b and 72d. The operation button 72f has a top surface thereof buried in the top surface of the housing 71, so as not to be inadvertently pressed by the user.

In front of the cross key 72a on the top surface of the housing 71, an operation button 72h is provided. The operation button 72h is a power switch for turning on and off the game apparatus body 5 by remote control. The operation button 72h also has a top surface thereof buried in the top surface of the housing 71, so as not to be inadvertently pressed by the user.

Behind the operation button 72c on the top surface of the housing 71, a plurality of LEDs 702 are provided. Here, a controller type (a number) is assigned to the core unit 70 such that the core unit 70 is distinguishable from other controllers. The LEDs 702 are used for, e.g., informing the user of the controller type currently set for the core unit 70. Specifically, a signal is transmitted from the wireless controller module 19 to the core unit 70 such that one of the plurality of LEDs 702, which corresponds to the controller type of the core unit 70, is lit up.

On the top surface of the housing 71, sound holes for outputting sounds from a later-described speaker (a speaker 706 shown in FIG. 5) to the external space are formed between the operation button 72b and the operation buttons 72e to 72g.

On the bottom surface of the housing 71, a recessed portion is formed. The recessed portion on the bottom surface of the housing 71 is formed in a position in which an index finger or middle finger of the user is located when the user holds the core unit 70 with one hand so as to point a front surface thereof to the markers 8L and 8R. On a slope surface of the recessed portion, an operation button 72i is provided. The operation button 72i is an operation section acting as, for example, a B button.

On the front surface of the housing 71, an image pickup element 743 that is a part of the imaging information calculation section 74 is provided. The imaging information calculation section 74 is a system for: analyzing image data of an image taken by the core unit 70; identifying an area having a high brightness in the image; and detecting a position of the center of gravity, the size, and the like of the area. The imaging information calculation section 74 has, for example, a maximum sampling period of approximately 200 frames/sec, and therefore can trace and analyze even a relatively fast motion of the core unit 70. A configuration of the imaging information calculation section 74 will be described later in detail. On the rear surface of the housing 71, a connector 73 is provided. The connector 73 is, for example, an edge connector, and is used for engaging and connecting the core unit 70 with a connection cable, for example.

In order to give a specific description below, a coordinate system set with respect to the core unit 70 will be defined. As shown in FIGS. 3 and 4, an X-axis, a Y-axis and a Z-axis, which are perpendicular to one another, are defined with respect to the core unit 70. Specifically, the longitudinal direction of the housing 71, which is the front-rear direction of the core unit 70, is defined as the Z-axis, and a direction along the Z-axis toward the front surface (a surface on which the imaging information calculation section is provided) of the core unit 70 is a Z-axis positive direction. The up-down direction of the core unit 70 is defined as the Y-axis, and a direction along the Y-axis toward the top surface (a surface on which the operation button 72a is provided) of the housing 71 is defined as a Y-axis positive direction. The left-right direction of the core unit 70 is defined as the X-axis, and a direction along the X-axis toward the right side surface (a side surface shown in FIG. 3) of the housing 71 is defined as an X-axis positive direction.

Figure 6:
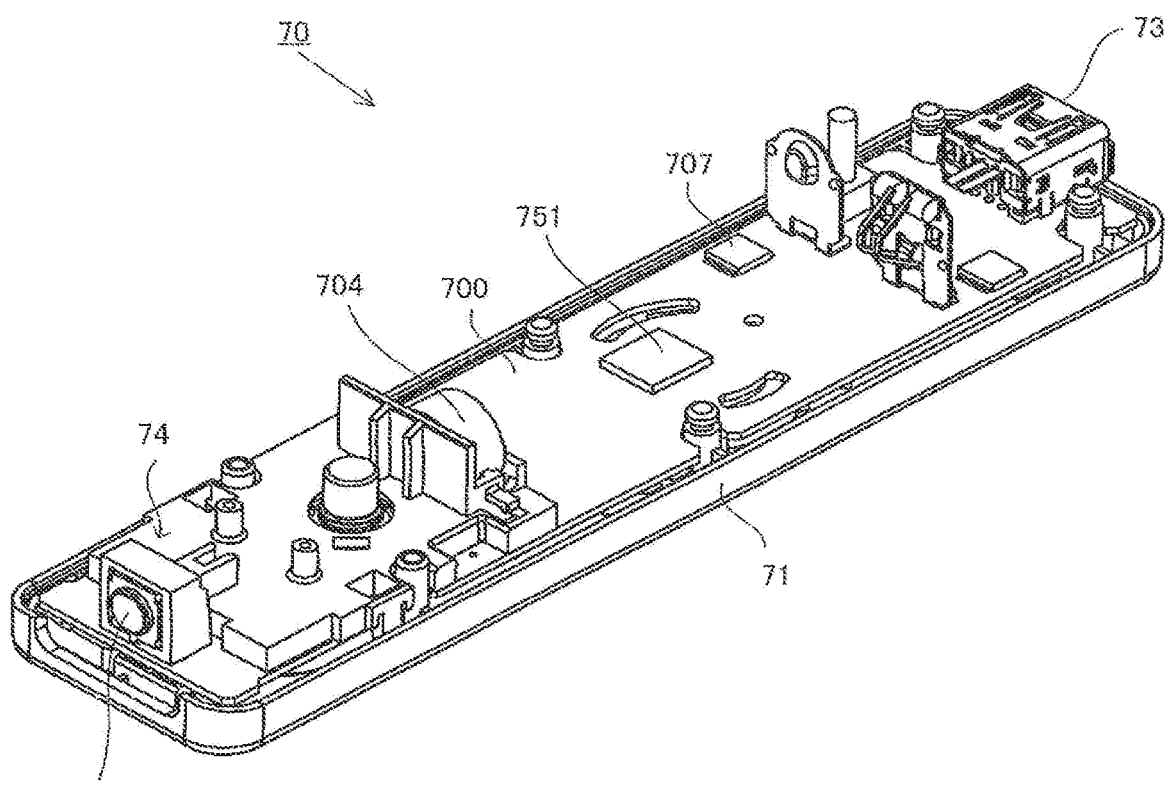
FIG. 6 is an isometric view, showing that a lower casing of the core unit 70 of FIG. 4 is removed.

Next, an internal structure of the core unit 70 will be described with reference to FIGS. 5 and 6. FIG. 5 is an isometric view, seen from a rear surface side of the core unit 70, showing that an upper casing (a part of the housing 71) of the core unit 70 is removed. FIG. 6 is an isometric view, seen from a front surface side of the core unit 70, showing that a lower casing (a part of the housing 71) of the core unit 70 is removed. Here, FIG. 6 is an isometric view showing a reverse side of a substrate 700 shown in FIG. 5.

As shown in FIG. 5, the substrate 700 is fixedly provided inside the housing 71. On a top main surface of the substrate 700, the operation buttons 72a to 72h, an acceleration sensor 701, the LEDs 702, an antenna 754 and the like are provided. These elements are connected to, for example, a microcomputer 751 (see FIGS. 6 and 7) by wiring (not shown) formed on the substrate 700 and the like. A wireless module 753 (see FIG. 7) and the antenna 754 allow the core unit 70 to act as a wireless controller. Inside the housing 71, a quartz oscillator, which is not shown, is provided, and the quartz oscillator generates a reference clock of the later-described microcomputer 751. Further, the speaker 706 and an amplifier 708 are provided on the top main surface of the substrate 700. The acceleration sensor 701 is provided, on the substrate 700, to the left side of the operation button 72d (i.e., provided not on a central part but on a peripheral part of the substrate 700). For this reason, in response to the core unit 70 having rotated around an axis of the longitudinal direction of the core unit 70, the acceleration sensor 701 is able to detect, in addition to a change in a direction of the gravitational acceleration, acceleration containing a centrifugal component, and the game apparatus body 5 or the like is able to determine, based on detected acceleration data, a motion of the core unit 70 by predetermined calculation with favorable sensitivity.

As shown in FIG. 6, at a front edge of the bottom main surface of the substrate 700, the imaging information calculation section 74 is provided. The imaging information calculation section 74 includes an infrared filter 741, a lens 742, the image pickup element 743, and an image processing circuit 744, which are located in said order from the front surface of the core unit 70. These elements are attached to the bottom main surface of the substrate 700. At a rear edge of the bottom main surface of the substrate 700, the connector 73 is attached. Further, a sound IC 707 and the microcomputer 751 are provided on the bottom main surface of the substrate 700. The sound IC 707 is connected to the microcomputer 751 and the amplifier 708 by wiring formed on the substrate 700 and the like, and outputs an audio signal via the amplifier 708 to the speaker 706 in response to sound data transmitted from the game apparatus body 5.

On the bottom main surface of the substrate 700, a vibrator 704 is attached. The vibrator 704 may be, for example, a vibration motor or a solenoid. The vibrator 704 is connected to the microcomputer 751 by wiring formed on the substrate 700 and the like, and is activated or deactivated in accordance with vibration data transmitted from the game apparatus body 5. The core unit 70 is vibrated by actuation of the vibrator 704, and the vibration is conveyed to the user's hand holding the core unit 70. Thus, a so-called vibration-feedback game is realized. Since the vibrator 704 is provided at a relatively forward position in the housing 71, the housing 71 held by the user significantly vibrates, and allows the user to easily feel the vibration.

Figure 7:
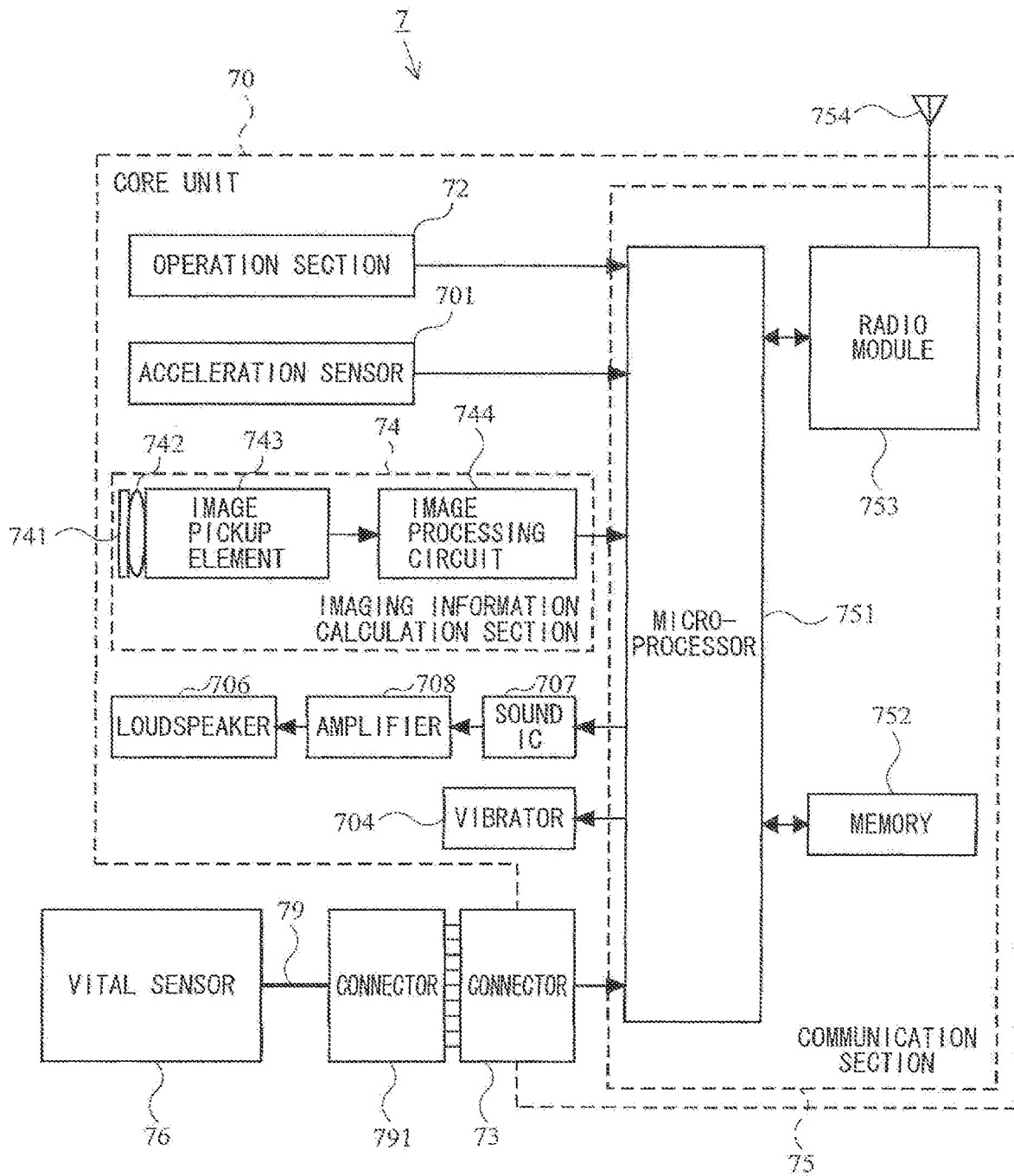
FIG. 7 is a block diagram showing an example of a configuration of the core unit 70 of FIG. 3.

Next, an internal configuration of the controller 7 will be described with reference to FIG. 7. FIG. 7 is a block diagram showing an example of the internal configuration of the controller 7.

As shown in FIG. 7, the core unit 70 includes the communication section 75 in addition to the above-described operation sections 72, the imaging information calculation section 74, the acceleration sensor 701, the vibrator 704, the speaker 706, the sound IC 707, and the amplifier 708. The vital sensor 76 is connected to the microcomputer 751 via the connection cable 79 and connectors 791 and 73.

The imaging information calculation section 74 includes the infrared filter 741, the lens 742, the image pickup element 743, and the image processing circuit 744. The infrared filter 741 allows, among lights incident thereon through the front surface of the core unit 70, only an infrared light to pass therethrough. The lens 742 condenses the infrared light having passed through the infrared filter 741, and outputs the condensed infrared light to the image pickup element 743. The image pickup element 743 is a solid-state image pickup element such as a CMOS sensor, CCD or the like. The image pickup element 743 takes an image of the infrared light condensed by the lens 742. In other words, the image pickup element 743 takes an image of only the infrared light having passed through the infrared filter 741. Then, the image pickup element 743 generates image data of the image. The image data generated by the image pickup element 743 is processed by the image processing circuit 744. Specifically, the image processing circuit 744 processes the image data obtained from the image pickup element 743, and detects a high brightness area of the image, and outputs, to the communication section 75, process result data indicating results of detecting, for example, position coordinates, a square measure and the like of the high brightness area. The imaging information calculation section 74 is fixed to the housing 71 of the core unit 70. An imaging direction of the imaging information calculation section 74 can be changed by changing a facing direction of the housing 71.

Preferably, the core unit 70 includes a triaxial (X-axis, Y-axis, and Z-axis) acceleration sensor 701. The triaxial acceleration sensor 701 detects linear acceleration in three directions, i.e., the up-down direction (the Y-axis shown in FIG. 3), the left-right direction (the X-axis shown in FIG. 3), and the front-rear direction (the Z-axis shown in FIG. 3). Alternatively, an accelerometer capable of detecting linear acceleration along at least one axis direction (e.g., Z-axis direction) may be used. As a non-limiting example, the acceleration sensor 701 may be of the type available from Analog Devices, Inc. or STMicroelectronics N.V. Preferably, the acceleration sensor 701 is an electrostatic capacitance or capacitance-coupling type that is based on silicon micro-machined MEMS (microelectromechanical systems) technology. However, any other suitable accelerometer technology (e.g., piezoelectric type or piezoresistance type) now existing or later developed may be used to provide the acceleration sensor 701.

Accelerometers, as used in the acceleration sensor 701, are only capable of detecting acceleration along a straight line (linear acceleration) corresponding to each axis of the acceleration sensor 701. In other words, the direct output of the acceleration sensor 701 is limited to signals indicative of linear acceleration (static or dynamic) along each of the three axes thereof. As a result, the acceleration sensor 701 cannot directly detect movement along a non-linear (e.g., arcuate) path, rotation, rotational movement, angular displacement, inclination, position, orientation or any other physical characteristic.

However, through processing by a computer such as a processor of the game apparatus (e.g., the CPU 10) or a processor of the controller (e.g., the microcomputer 751) based on the acceleration signals outputted from the acceleration sensor 701, additional information relating to the core unit 70 can be inferred or calculated (determined), as one skilled in the art will readily understand from the description herein.

For example, when the processing is performed by the computer on the assumption that the core unit 70 having the acceleration sensor 701 mounted therein is in a static state (i.e., when the processing is performed assuming that acceleration detected by the acceleration sensor is only the gravitational acceleration), if the core unit 70 is in fact in a static state, the detected acceleration is used to determine whether or not the core unit 70 is inclined with respect to the direction of gravity or how many degrees the core unit 70 is inclined with respect to the direction of gravity. More specifically, when a state where a detection axis of the acceleration sensor 701 extends in a vertically downward direction is set as a standard state, it is possible to determine whether or not the core unit 70 is inclined with respect to the vertically downward direction, based on whether or not 1 G (gravitational acceleration) is being applied in a direction along the detection axis of the acceleration sensor 701. It is also possible to determine how many degrees the core unit 70 is inclined with respect to the vertically downward direction, based on the magnitude of acceleration applied in the direction along the detection axis. In addition, in the case where the acceleration sensor 701 is capable of detecting acceleration along multiple axis directions, it is possible to determine in detail how many degrees the core unit is inclined with respect to the direction of gravity, through processing of acceleration signals detected for each axis. In this case, a processor may perform processing, based on an output from the acceleration sensor 701, for calculating data indicating an inclination angle of the core unit 70. Alternatively, processing may be performed so as to infer a rough inclination of the core unit 70 based on the output from the acceleration sensor 701 without performing the processing for calculating data indicating an inclination angle. In this manner, the acceleration sensor 701 can be used in combination with the processor to determine an inclination, orientation or position of the core unit 70.

On the other hand, on the assumption that the acceleration sensor 701 is in a dynamic state, the acceleration sensor 701 detects acceleration corresponding to a movement of the acceleration sensor 701 in addition to a gravitational acceleration component. Thus, it is possible to determine, for example, a direction of the movement of the core unit 70 by eliminating the gravitational acceleration component through predetermined processing. More specifically, various movements and/or positions of the core unit 70 can be calculated through processing of the acceleration signals generated by the acceleration sensor 701 when the core unit 70 including the acceleration sensor 701 is subjected to dynamic acceleration by the hand of a user. It is noted that even on the assumption that the acceleration sensor 701 is in a dynamic state, it is possible to determine an inclination of the core unit 70 with respect to the direction of gravity, by eliminating acceleration corresponding to a movement of the acceleration sensor 701 through predetermined processing.

In another example, the acceleration sensor 701 may include an embedded signal processor or other type of dedicated processor for performing any desired processing of the acceleration signals outputted from the accelerometers therein prior to outputting signals to the microcomputer 751. For example, the embedded or dedicated processor could convert the detected acceleration signal to a corresponding inclination angle (or into other preferred parameter) when the acceleration sensor 701 is intended to detect static acceleration (e.g., gravitational acceleration). Data indicating the acceleration detected by the acceleration sensor 701 is outputted to the communication section 75.

In further another example, the acceleration sensor 701 may be replaced with a gyro-sensor of any suitable technology incorporating, for example, a rotating or vibrating element. Exemplary MEMS gyro-sensors that may be used in this embodiment are available from Analog Devices, Inc. Unlike the linear acceleration sensor 701, a gyro-sensor is capable of directly detecting rotation (or angular rate) around an axis defined by the gyroscopic element (or elements) therein. Thus, due to the fundamental differences between a gyro-sensor and an acceleration sensor, corresponding changes need to be made to the processing operations that are performed on the output signals from these devices depending on which device is selected for a particular application.

Specifically, when a gyro-sensor is used instead of an acceleration sensor to calculate an inclination and orientation, significant changes are necessary. More specifically, when a gyro-sensor is used, the value of inclination is initialized at the start of detection. Then, data on angular velocity which is outputted from the gyro-sensor is integrated. Next, a change amount in inclination from the value of inclination previously initialized is calculated. In this case, the calculated inclination is obtained as a value corresponding to an angle. In contrast, when an acceleration sensor is used to calculate the inclination, the inclination is calculated by comparing the value of the gravitational acceleration of each axial component with a predetermined reference. Therefore, the calculated inclination can be represented as a vector. Thus, without initialization, an absolute direction detected using an accelerometer can be obtained. The type of the value calculated as an inclination is also different between a gyro-sensor and an acceleration sensor; i.e., the value is an angle when a gyro-sensor is used and is a vector when an acceleration sensor is used. Therefore, when a gyro-sensor is used instead of an acceleration sensor, data on inclination also needs to be processed by a predetermined conversion that takes into account the fundamental differences between these two devices. Due to the fact that the nature of gyroscopes is known to one skilled in the art, as well as the fundamental differences between accelerometers and gyroscopes, further details are not provided herein. While gyro-sensors provide certain advantages due to their ability to directly detect rotation, acceleration sensors are generally more cost-effective as compared with the gyro-sensors when used for the controller of the present embodiment.

The communication section 75 includes the microcomputer 751, a memory 752, the wireless module 753, and the antenna 754. The microcomputer 751 controls the wireless module 753 that wirelessly transmits transmission data, while using the memory 752 as a storage area during processing. The microcomputer 751 also controls operations of the sound IC 707 and the vibrator 704 in accordance with data which the wireless module 753 has received from the game apparatus body 5 via the antenna 754. The sound IC 707 processes sound data or the like which is transmitted from the game apparatus body 5 via the communication section 75. Further, the microcomputer 751 activates the vibrator 704 in accordance with vibration data or the like (e.g., a signal for causing the vibrator 704 to be ON or OFF) which is transmitted from the game apparatus body 5 via the communication section 75.

Operation signals from the operation sections 72 provided on the core unit 70 (key data), acceleration signals from the acceleration sensor 701 with respect to the three axial directions (X-, Y- and Z-axis direction acceleration data), and the process result data from the imaging information calculation section 74, are outputted to the microcomputer 751. Also, biological signals (biological information data) provided from the vital sensor 76 are outputted to the microcomputer 751 via the connection cable 79. The microcomputer 751 temporarily stores inputted data (the key data, the X-, Y- and Z-axis direction acceleration data, the process result data, and the biological information data) in the memory 752 as transmission data to be transmitted to the wireless controller module 19. Here, wireless transmission from the communication section 75 to the wireless controller module 19 is performed at predetermined time intervals. Since game processing is generally performed at a cycle of ⅓₀ sec, the wireless transmission needs to be performed at a shorter cycle. Specifically, game processing is performed at a cycle of 16.7 ms (⅙₀ sec), and a transmission interval of the communication section 75 configured using the Bluetooth (registered trademark) technology is 5 ms. When a timing of performing transmission to the wireless controller module 19 arrives, the microcomputer 751 outputs, to the wireless module 753, the transmission data stored in the memory 752 as a series of pieces of operation information. The wireless module 753 uses, for example, the Bluetooth (registered trademark) technology to radiate, using a carrier wave having a predetermined frequency, a radio signal from the antenna 754, the radio signal indicating the series of pieces of operation information. Thus, the key data from the operation sections 72 provided on the core unit 70, the X-, Y- and Z-axis direction acceleration data from the acceleration sensor 701, the process result data from the imaging information calculation section 74, and the biological information data from the vital sensor 76, are transmitted from the core unit 70. The wireless controller module 19 of the game apparatus body 5 receives the radio signal, and the game apparatus body 5 demodulates or decodes the radio signal to obtain the series of pieces of operation information (the key data, the X-, Y- and Z-axis direction acceleration data, the process result data, and the biological information data). In accordance with the series of pieces of obtained operation information and the game program, the CPU 10 of the game apparatus body 5 performs game processing. In the case where the communication section 75 is configured using the Bluetooth (registered trademark) technology, the communication section 75 can have a function of receiving transmission data wirelessly transmitted from other devices.

Figure 8:
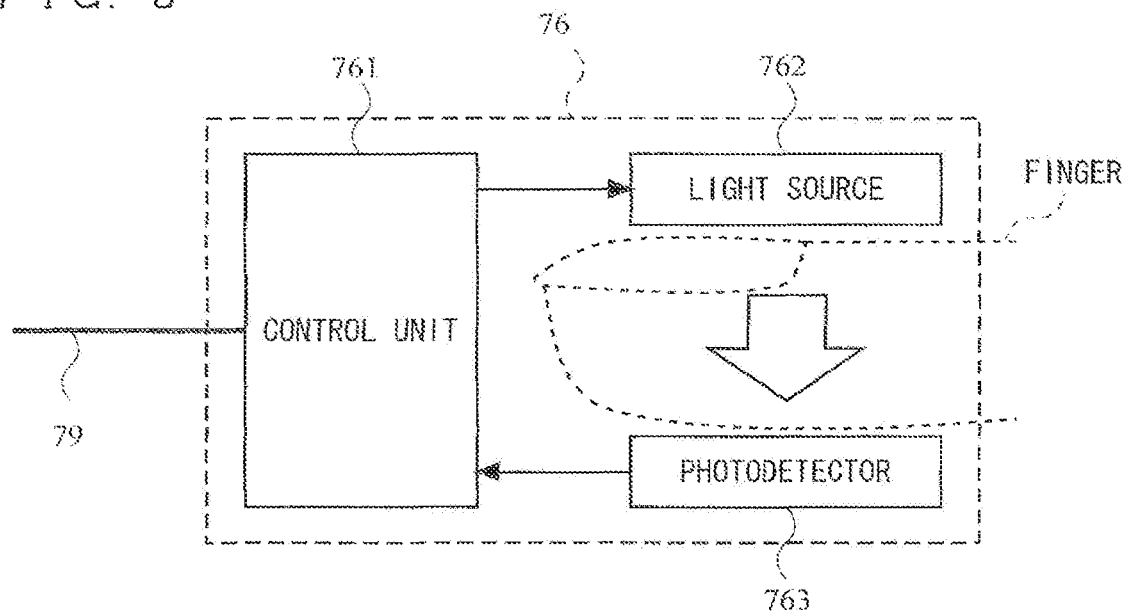
FIG. 8 is a block diagram showing an example of a configuration of a vital sensor 76.
Figure 9:
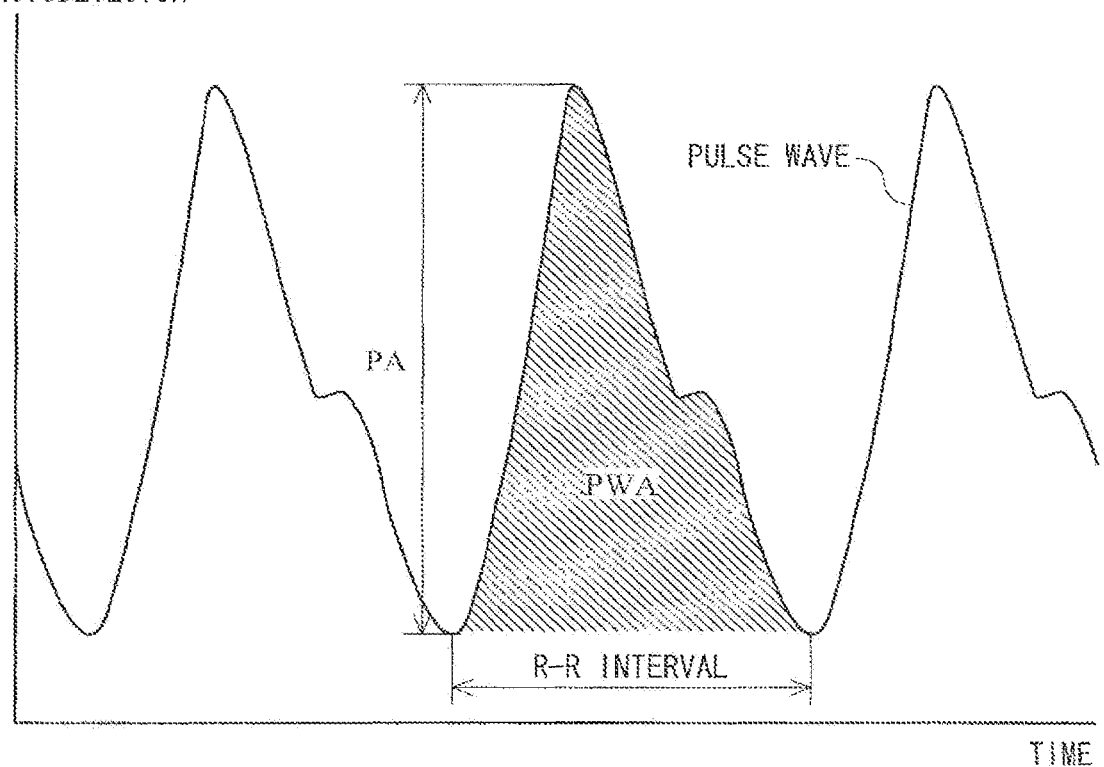
FIG. 9 is a diagram showing an example of pulse wave information which is an example of biological information outputted from the vital sensor 76.

Next, with reference to FIGS. 8 and 9, the vital sensor 76 will be described. Note that FIG. 8 is a block diagram showing an example of a configuration of the vital sensor 76. FIG. 9 is a diagram showing pulse wave information which is an example of biological information outputted from the vital sensor 76.

In FIG. 8, the vital sensor 76 includes a control unit 761, a light source 762, and a photodetector 763.

The light source 762 and the photodetector 763 constitutes a transmission-type digital-plethysmography sensor, which is an example of a sensor which obtains a biological signal of the user. The light source 762 includes, for example, an infrared LED which emits infrared light having a predetermined wavelength (e.g., 940 nm) toward the photodetector 763. On the other hand, the photodetector 763, which includes, for example, an infrared photoregister, senses light emitted by the light source 762, depending on the wavelength of the emitted light. The light source 762 and the photodetector 763 are arranged, facing each other, with a predetermined gap (hollow space) being interposed therebetween.

Here, hemoglobin which exists in human blood absorbs infrared light. For example, a portion (e.g., a fingertip) of the body of the user is inserted in the gap between the light source 762 and the photodetector 763. In this case, infrared light emitted from the light source 762 is partially absorbed by hemoglobin existing in the inserted fingertip before being sensed by the photodetector 763. Arteries in the human body pulsate, and therefore, the thickness (blood flow rate) of the artery varies depending on the pulsation. Therefore, similar pulsation occurs in arteries in the inserted fingertip, and the blood flow rate varies depending on the pulsation, so that the amount of infrared light absorption also varies depending on the blood flow rate. Specifically, as the blood flow rate in the inserted fingertip increases, the amount of light absorbed by hemoglobin also increases and therefore the amount of infrared light sensed by the photodetector 763 relatively decreases. Conversely, as the blood flow rate in the inserted fingertip decreases, the amount of light absorbed by hemoglobin also decreases and therefore the amount of infrared light sensed by the photodetector 763 relatively increases. The light source 762 and the photodetector 763 utilize such an operating principle, i.e., converts the amount of infrared light sensed by the photodetector 763 into a photoelectric signal to detect pulsation (hereinafter referred to as a pulse wave) of the human body. For example, as shown in FIG. 9, when the blood flow rate in the inserted fingertip increases, the detected value of the photodetector 763 increases, and when the blood flow rate in the inserted fingertip decreases, the detected value of the photodetector 763 decreases. Thus, a pulse wave portion in which the detected value of the photodetector 763 rises and falls is generated as a pulse wave signal. Note that, in some circuit configuration of the photodetector 763, a pulse wave signal may be generated in which, when the blood flow rate in the inserted fingertip increases, the detected value of the photodetector 763 decreases, and when the blood flow rate in the inserted fingertip decreases, the detected value of the photodetector 763 increases.

The control unit 761 includes, for example, a MicroController Unit (MCU). The control unit 761 controls the amount of infrared light emitted from the light source 762. The control unit 761 also performs A/D conversion with respect to a photoelectric signal (pulse wave signal) outputted from the photodetector 763 to generate pulse wave data (biological information data). Thereafter, the control unit 761 outputs the pulse wave data (biological information data) via the connection cable 79 to the core unit 70.

Next, an overview of a process performed by the game apparatus body 5 will be described with reference to FIGS. 10 to 18 before a specific description thereof will be given. Note that FIGS. 10 to 18 are diagrams showing a series of images displayed on the monitor 2.

Figure 10:
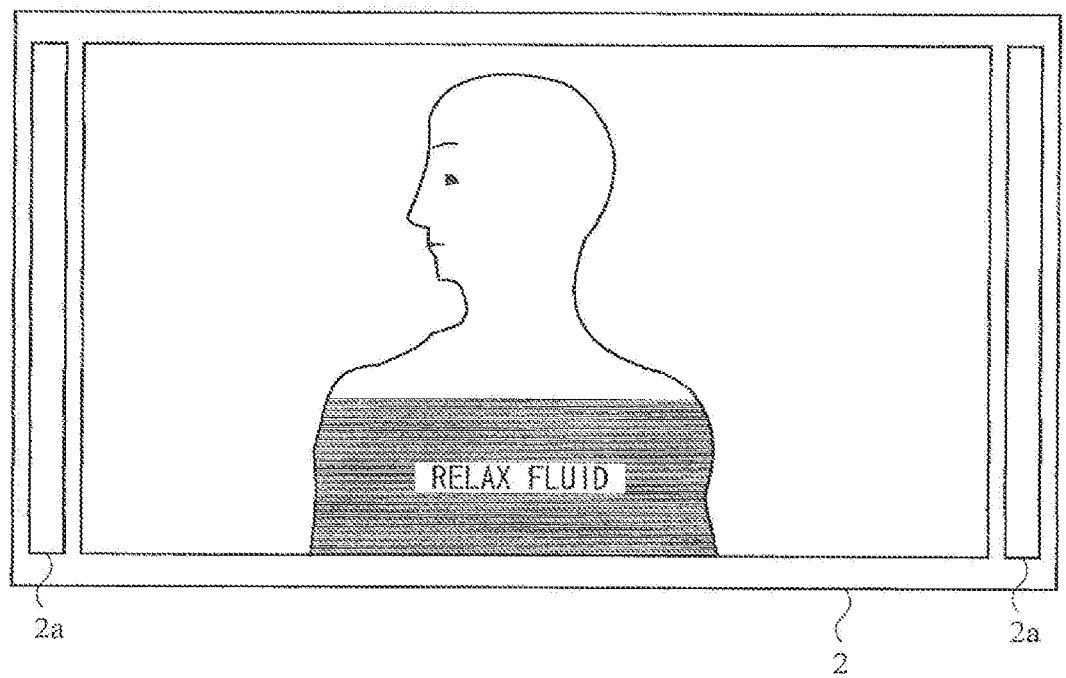
FIG. 10 is a diagram showing an example of an image displayed on a monitor 2.

In FIG. 10, the monitor 2 displays a current biological state of the user who is using the vital sensor 76. For example, in FIG. 10, an activity level of the parasympathetic nervous system of the user, which is a representative level of the autonomic nervous system, is displayed as an amount of relax fluid. The amount of relax fluid is calculated based on a heart rate variance coefficient (coefficient of variance of R-R interval (CVRR)) of the user. For example, the heart rate variance coefficient is calculated using cardiac cycles (R-R intervals; see FIG. 9) over past 100 pulses indicated by a pulse wave obtained from the vital sensor 76. Specifically, the heart rate variance coefficient is calculated by:

heart rate variance coefficient=(the standard deviation of the R-R intervals of 100 pulses/the average of the R-R intervals of 100 pulses)×100

By changing the amount (e.g., a surface level) of the relax fluid, depending on the calculated heart rate variance coefficient, the current biological information is presented to the user.

Figure 11:
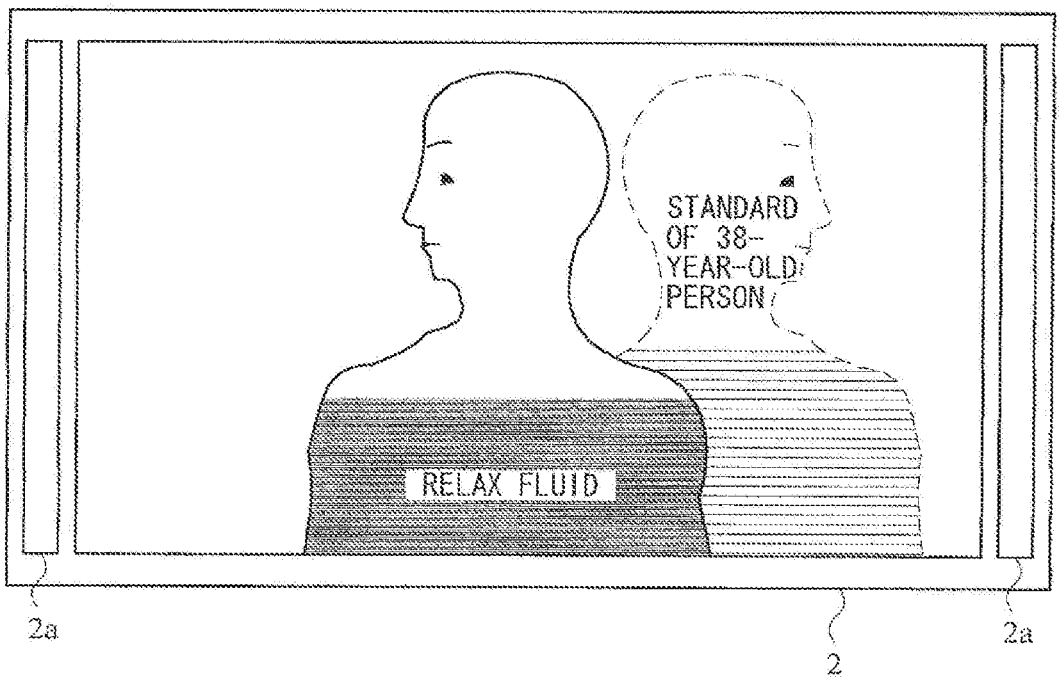
FIG. 11 is a diagram showing an example of an image displayed on the monitor 2.

Next, in FIG. 11, the monitor 2 displays a standard value of the relax fluid amount for the same age as that of the user for comparison with the current relax fluid amount of the user. Here, the relax fluid amount decreases as the parasympathetic nervous system of the user is activated. Specifically, if the relax fluid amount is lower in the absence of exercise load to the user, it is considered that the user's autonomic nervous system is not balanced. However, since the relax fluid amount tends to decrease with age, the standard relax fluid amount of the same age is displayed along with the current relax fluid amount so as to enable the user to easily evaluate the relative activity level of their parasympathetic nervous system.

Figure 12:
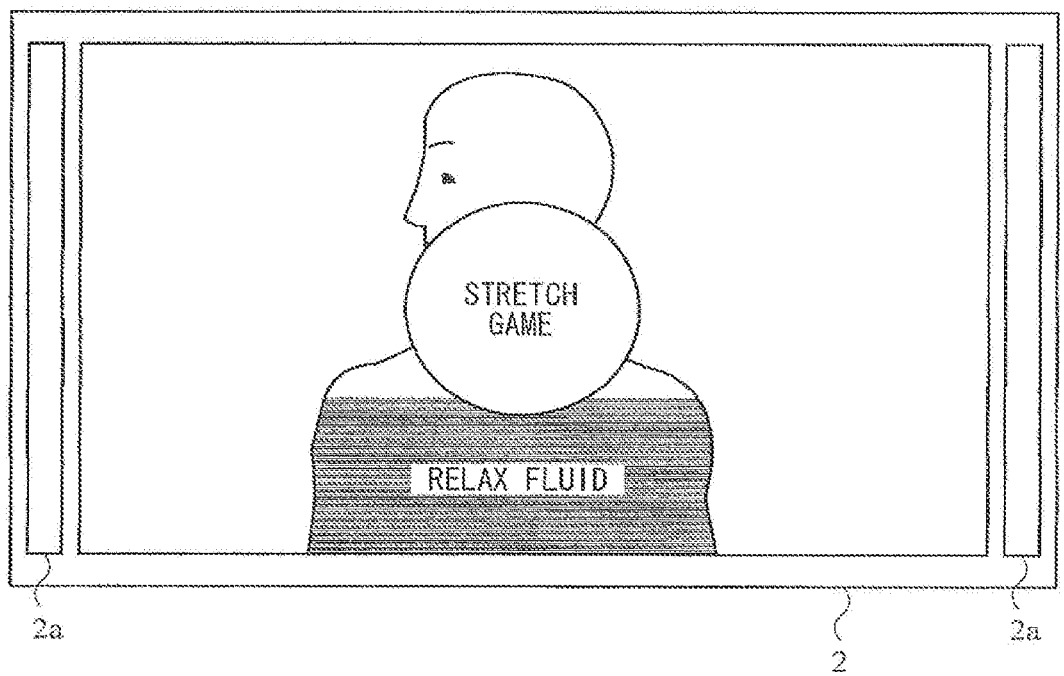
FIG. 12 is a diagram showing an example of an image displayed on the monitor 2.

Next, in FIG. 12, the monitor 2 presents a game for improving a displayed biological state of the user. For example, a stretch game which increases the flexibility of the user is a means of instantly increasing the relax fluid amount, and therefore, is displayed as an option to the user on the monitor 2. When the user selects and decides execution of the presented stretch game, the screen of the monitor 2 transitions to the stretch game.

After transition to the stretch game, the monitor 2 displays explanations of an operation attitude or an operation method which the user should perform when playing the game. For example, in the example of FIG. 13, an attitude that the vital sensor 76 is attached to a finger and the core unit 70 is sandwiched between both hands with both elbows sticking out leftward and rightward in a longitudinal direction of the core unit 70, is displayed as an operation attitude which the user should take in the stretch game. The monitor 2 also displays an operation method, i.e., "Please incline the core unit 70 to match its inclination angle to the slope of the ground, assuming the screen is a mirror." The monitor 2 also displays an operation method, i.e., "Please breathe in synchronization with rising and falling of the ceiling." Thus, the user can find out an operation attitude and an operation method, such as those shown in FIG. 13, by viewing those displayed on the screen.

Figure 14:
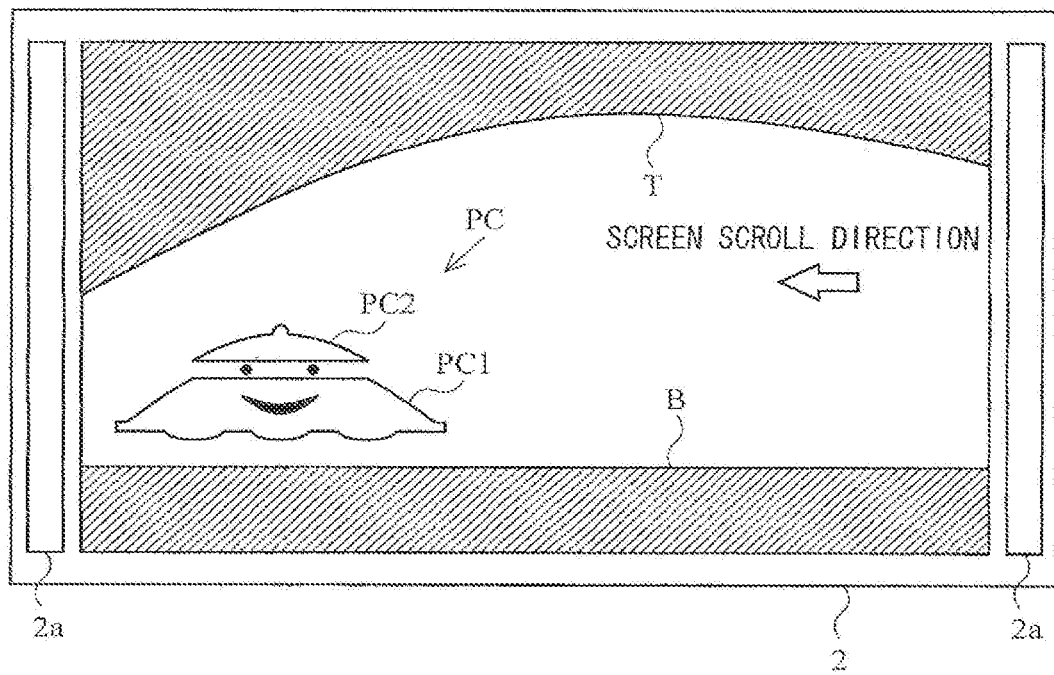
FIG. 14 is a diagram showing an example of an image displayed on the monitor 2.

As shown in FIG. 14, in the stretch game, for example, a game is performed in which a player character PC moves or behaves based on a biological signal (pulse wave signal) of the user and a motion or an attitude (an inclination of the core unit 70) of the user. The user has to cause the player character PC to fly in a space (e.g., a cave) between a ceiling T and a ground B which are, for example, scrolled from the left to the right in the virtual game world. In this case, the ceiling T and the ground B are obstacles in the way of the player character PC flying in the space. The player character PC includes a first player character PC1, and a second player character PC2 provided on the first player character PC1, which are separable.

Figure 15:
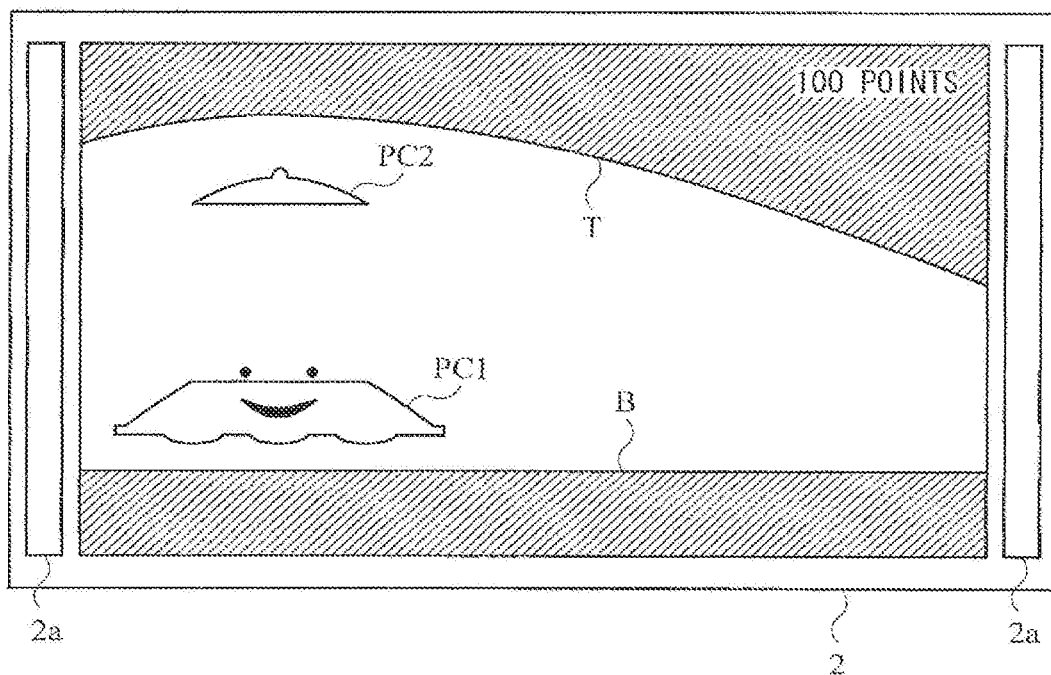
FIG. 15 is a diagram showing an example of an image displayed on the monitor 2.

In FIG. 15, the second player character PC2 can be moved up, where a maximum height of the second player character PC2 is limited to a height of the ceiling T (the height is measured with reference to the first player character PC1). Here, the second player character PC2 is moved up and down, depending on a respiratory state of the user. For example, the second player character PC2 is moved up with respect to the first player character PC1 when the user breathes out air or exhales, and is moved down toward the first player character PC1 when the user breathes in air or inhales. In this embodiment, a heart rate HR of the user is calculated using the pulse wave signal, and if the heart rate HR is increasing, it is determined that the user is inhaling, and if the heart rate HR is decreasing, it is determined that the user exhaling. The heart rate HR is represented by the number of heart beats per 60 seconds. In this embodiment, the heart rate HR is calculated by dividing 60 seconds by a cardiac cycle (R-R interval; e.g., the time from one minimum value of a pulse wave to the next minimum value; see FIG. 9).

Rising and falling of the ceiling T are calculated based on a frequency of respiration of the user. For example, in this embodiment, a current frequency of respiration of the user is calculated based on a frequency at which the heart rate HR of the user rises and falls. The frequency of rising and falling of the ceiling T is adjusted so that the respiration frequency is slowed to a predetermined fraction thereof (e.g., 80%). If the second player character PC2 contacts the ceiling T, the score of the stretch game is reduced. Specifically, the user has to breathe in a manner which reduces their respiration frequency to 80%, i.e., gradually reduces their respiration frequency, while moving the second player character PC2 up and down in synchronization with rising and falling of the ceiling T.

Figure 13:
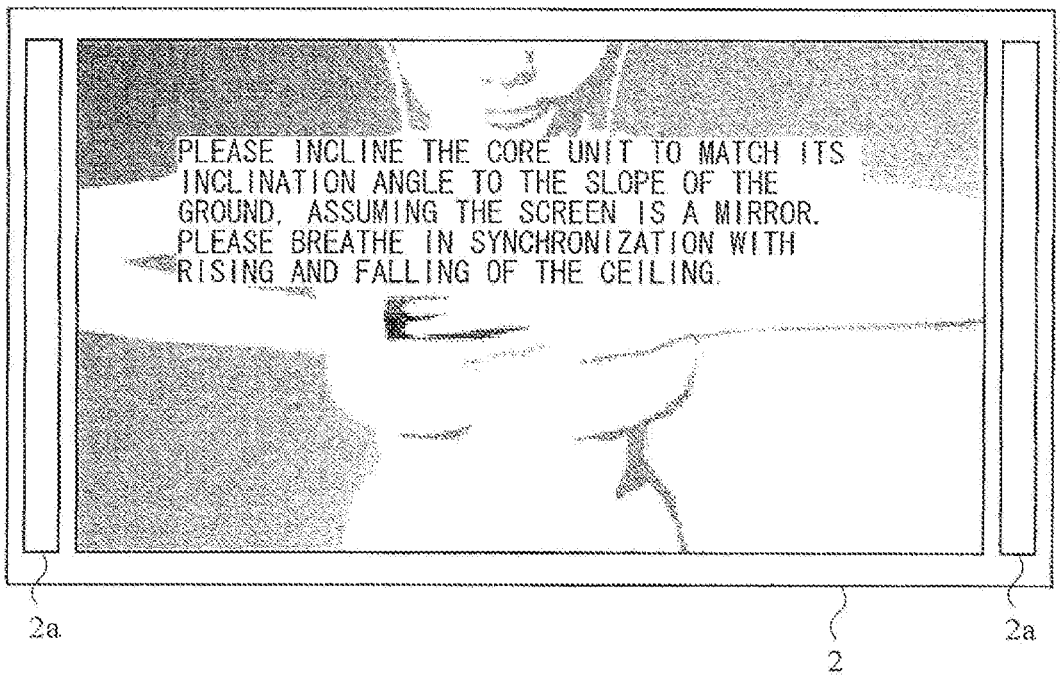
FIG. 13 is a diagram showing an example of an image displayed on the monitor 2.
Figure 16:
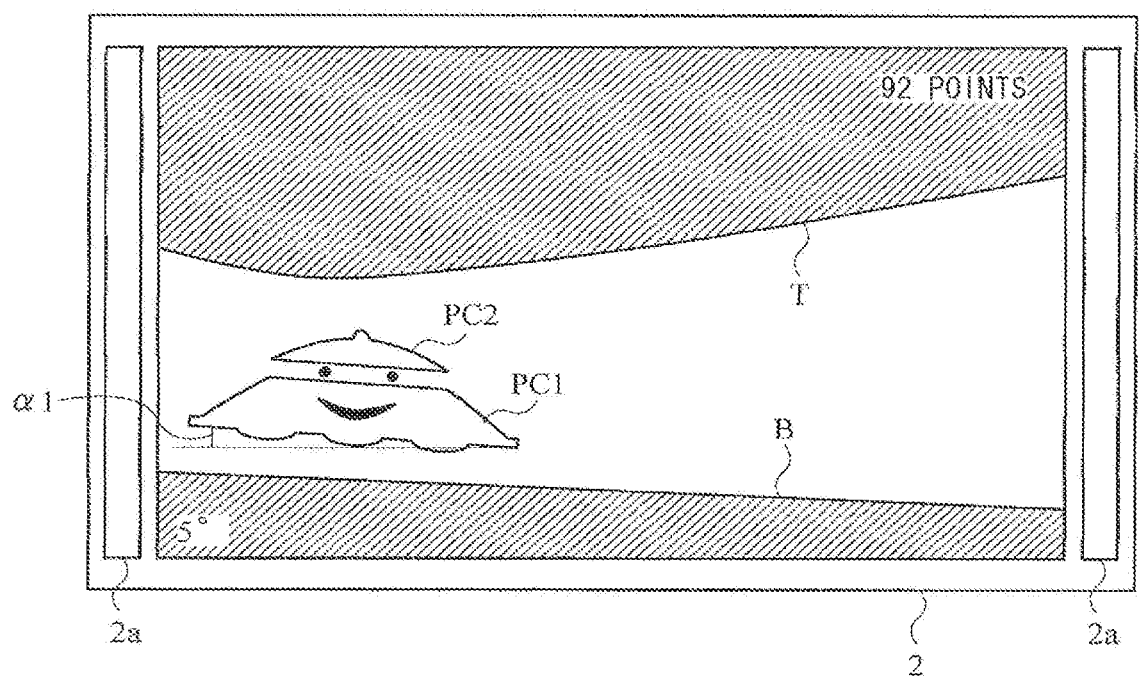
FIG. 16 is a diagram showing an example of an image displayed on the monitor 2.
Figure 16:
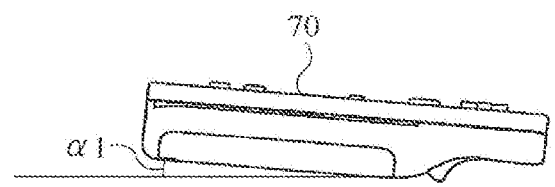

Referring to FIG. 16, the player character PC can fly obliquely along the ground B. Here, the player character PC inclines its flying attitude, depending on the inclination of the core unit 70. For example, when the user in an operation attitude as shown in FIG. 13 inclines the core unit 70 to the right (as the user faces the monitor 2) at an angle of al, the displayed player character PC is also inclined to the right at an angle of al in synchronization with the act of inclining. Also, referring to FIG. 17, when the user in an operation attitude as shown in FIG. 13 inclines the core unit 70 to the right (as the user faces the monitor 2) at an angle of α2, the displayed player character PC is also inclined to the right at an angle of α2 in synchronization with the act of inclining. In other words, the user feels like they incline the player character PC by inclining the core unit 70.

Figure 17:
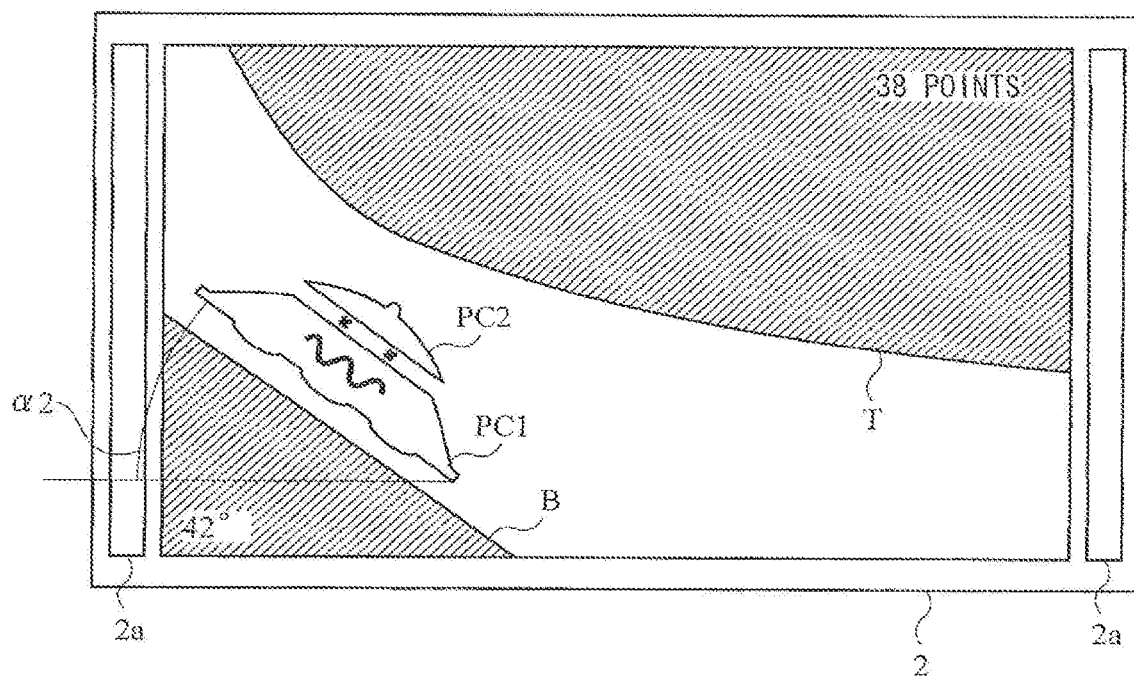
FIG. 17 is a diagram showing an example of an image displayed on the monitor 2.
Figure 17:
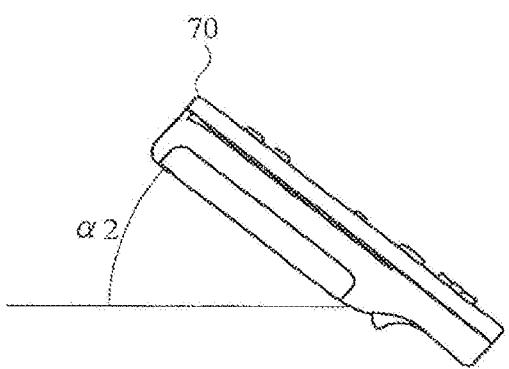
Figure 18:
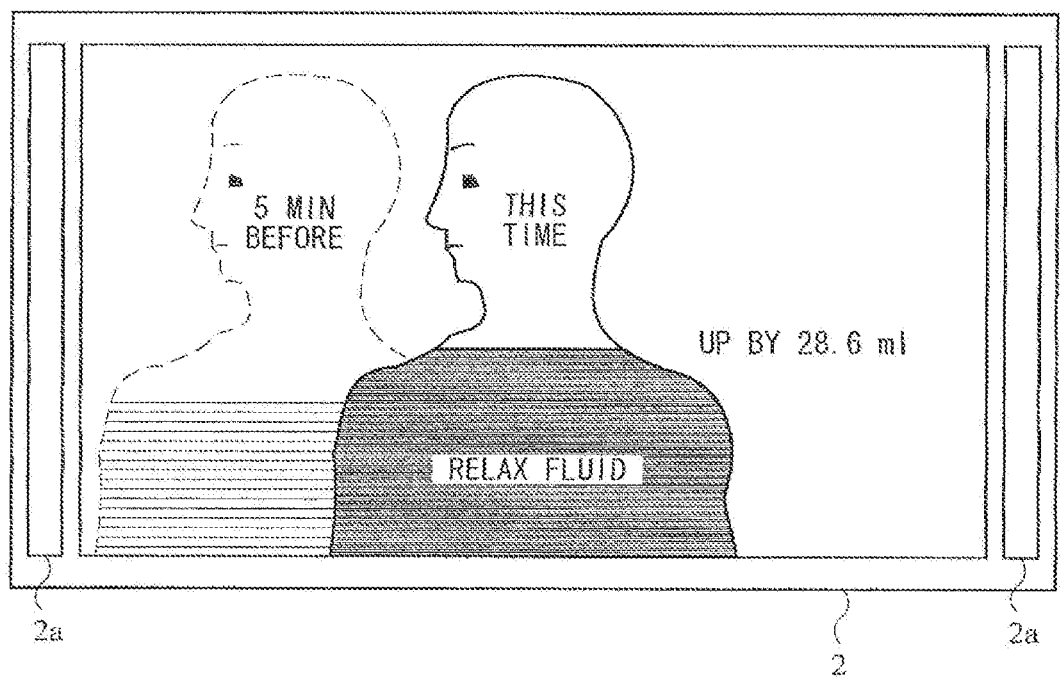
FIG. 18 is a diagram showing an example of an image displayed on the monitor 2.

In FIG. 17, when the slope (angle) of the ground B increases with time, then if the player character PC contacts the ground B, the score of the stretch game is reduced. The user has to incline the core unit 70 at an angle similar to the slope of the ground B so as to incline the player character PC to match the inclination angle to the slope of the ground B. In other words, the user has to do stretching movements, such as bending or twisting a portion of their body at which the core unit 70 is held or attached. The slope of the ground B is fixed to an inclination angle as it is when the user has difficulty in further inclining the core unit 70. For example, in this embodiment, a pulse wave amplitude PA (e.g., a difference between one minimum value of a pulse wave and the next minimum value; see FIG. 9) obtained from the pulse wave signal is used to determine a level of difficulty or easiness of the user, and a color or countenance of the player character PC is changed, depending on the difficulty or easiness level.

In the example of FIG. 16, the ground B is displayed which is inclined to the right at an inclination angle of 5°. If the user inclines the core unit 70 to the right (as the user faces the monitor 2) at an angle of a1 (e.g., 5°) to match the inclination angle to the slope of the ground B, the displayed player character PC is also inclined to the right at an angle of a1 (e.g., 5°) in synchronization with the act of inclining. In this case, since it is still easy for the user to do so, the displayed player character PC has calm countenance. On the other hand, in the example of FIG. 17 the displayed ground B is inclined to the right at an inclination angle of 42°, and if the user inclines the core unit 70 to the right (as the user faces the monitor 2) at an angle of α2 (e.g., 42°) to match the inclination angle to the slope of the ground B, the displayed player character PC is also inclined to the right at an angle of α2 (e.g., 42°) in synchronization with the act of inclining. In this case, the user has much difficulty, so that the displayed player character PC has unpleasant or painful countenance.

For example, a user's condition that their pulse wave amplitude PA is 90% or more as compared to that at the start of the stretch game, is determined as "the user does not have difficulty." A user's condition that their pulse wave amplitude PA is reduced to 50% to 90% as compared to that at the start of the stretch game, is determined as "the user has difficulty." Moreover, a user's condition that their pulse wave amplitude PA is reduced to 50% or less as compared to that at the start of the stretch game, is determined as "the user has much difficulty." A user's condition as it is when the pulse wave amplitude PA reaches 50% or less is determined as a limit for the user, and the inclination angle at this time (limit inclination angle) is considered as a measure for calculating the pliancy of the user's body.

After the stretch game is ended, a current relax fluid amount of the user is calculated again. Thereafter, referring to FIG. 18, the monitor 2 displays a relax fluid amount before the stretch game (denoted as "5 min before" in FIG. 18) in addition to the current relax fluid amount (user's relax fluid amount after the stretch game). Moreover, an increase or a decrease in relax fluid amount after the stretch game is displayed as a numerical value. For example, in this embodiment, a heart rate variance coefficient before the stretch game of the user is compared with a heart rate variance coefficient after the stretch game, and a value obtained by multiplying a difference therebetween by 10 is displayed as an increase or a decrease in volume (ml).

Moreover, a value indicating the pliancy of the user's body may be displayed after the end of the stretch game. For example, the limit inclination angle is used to display the user's pliancy (pliancy score). Specifically, the user's limit inclination angle is compared with an ideal inclination angle in the stretch game, and the user's pliancy (pliancy score) is calculated and displayed based on a difference therebetween.

Next, game processing performed in the game system 1 will be described in detail. Firstly, referring to FIG. 19, main data used in game processing will be described. Note that FIG. 19 is a diagram showing an example of main data and programs stored in the external main memory 12 and/or the internal main memory 35 (hereinafter the two main memories is collectively referred to as a main memory) of the game apparatus body 5.

Figure 19:
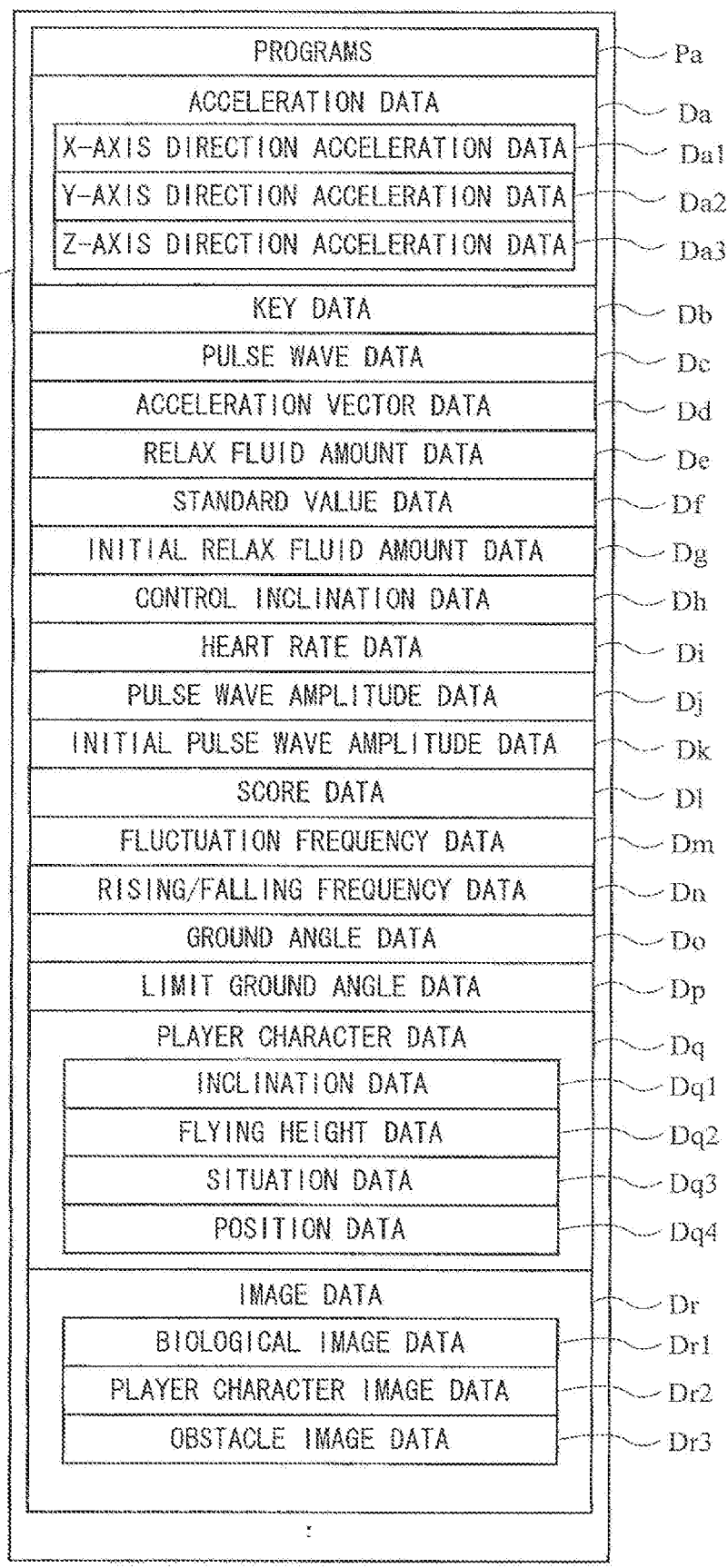
FIG. 19 is a diagram showing an example of main data and a program stored in a main memory of the game apparatus body 5.

As shown in FIG. 19, a data storing area of the main memory stores acceleration data Da, key data Db, pulse wave data Dc, acceleration vector data Dd, relax fluid amount data De, standard value data Df, initial relax fluid amount data Dg, controller inclination data Dh, heart rate data Di, pulse wave amplitude data Dj, initial pulse wave amplitude data Dk, score data Dl, fluctuation frequency data Dm, rising/falling frequency data Dn, ground angle data Do, limit ground angle data Dp, player character data Dq, image data Dr, and the like. Note that the main memory stores, in addition to data included in the information of FIG. 19, data required for game processing, such as data (position data, etc.) relating to objects and the like appearing in the game other than the player character PC, data (background data, etc.) relating to the virtual game world, and the like. Moreover, a program storing area of the main memory stores various programs Pa included in a game program.

The acceleration data Da indicates an acceleration of the core unit 70. Acceleration data included in a series of pieces of operation information which are transmitted as transmission data from the core unit 70 is stored as the acceleration data Da into the main memory. The acceleration data Da includes X-axis direction acceleration data Da1 indicating an acceleration which is detected with respect to an X-axis component by the acceleration sensor 701, Y-axis direction acceleration data Da2 indicating an acceleration which is detected with respect to a Y-axis component, and Z-axis direction acceleration data Da3 indicating an acceleration which is detected with respect to a Z-axis component. Note that the wireless controller module 19 included in the game apparatus body 5 receives acceleration data included in operation information transmitted in predetermined cycles (e.g., 1/200 sec) from the core unit 70, and stores the acceleration data into a buffer (not shown) included in the wireless controller module 19. Thereafter, acceleration data stored in the buffer is read out on a frame-by-frame basis (one frame corresponds to a game processing cycle (e.g., 1/60 sec)), and the acceleration data Da in the main memory is updated with the acceleration data.

In this case, the cycle of reception of operation information is different from the processing cycle, and therefore, a plurality of pieces of operation information received at a plurality of timings are stored in the buffer. In a description below of the process, it is assumed that only the latest one of a plurality of pieces of operation information received at a plurality of timings is invariably used to perform processing in each step described below before control proceeds to the next step.

Although it is assumed in a process flow described below that the acceleration data Da is updated on a frame-by-frame basis (one frame corresponds to the game processing cycle), the acceleration data Da may be updated in other process cycles. For example, the acceleration data Da may be updated in transmission cycles of the core unit 70, and the acceleration data Da thus updated may be used in game processing cycles. In this case, the cycle in which the acceleration data Da1 to Da3 are stored as the acceleration data Da is different from the game processing cycle.

The key data Db indicates that the operation sections 72 of the core unit 70 each have been operated. Key data included in a series of pieces of operation information which are transmitted as transmission data from the core unit 70 is stored as the key data Da into the main memory. Note that a method of updating the key data Db is similar to that of the acceleration data Da and will not be described in detail.

The pulse wave data Dc indicates a pulse wave signal having a required time length obtained from the vital sensor 76. Pulse wave data included in a series of pieces of operation information which are transmitted as transmission data from the core unit 70 is stored as the pulse wave data Dc into the main memory. Note that a history of a pulse wave signal having a time length required in a process described below is stored as the pulse wave data Dc into the main memory, and is updated as appropriate in response to reception of operation information.

The acceleration vector data Dd indicates an acceleration vector which is calculated using an acceleration indicated by the X-axis direction acceleration data Da1, the Y-axis direction acceleration data Da2, and the Z-axis direction acceleration data Da3. Data indicating a direction and a magnitude of an acceleration applied to the core unit 70 is stored as the acceleration vector data Dd in the main memory.

The relax fluid amount data De indicates a relax fluid amount which is calculated using a current heart rate variance coefficient of the user. The standard value data Df indicates a standard value of a relax fluid amount for each age which is previously statistically calculated. The initial relax fluid amount data Dg indicates a relax fluid amount of the user which is calculated before the start of the stretch game.

The controller inclination data Dh indicates an inclination of the core unit 70 with respect to a direction of gravity. The heart rate data Di indicates a history of heart rates HR (e.g., a value obtained by dividing 60 sec by a cardiac cycle (R-R interval)) over a predetermined period of time of the user. The pulse wave amplitude data Dj indicates a history of pulse wave amplitudes PA over a predetermined period of time of the user. The initial pulse wave amplitude data Dk indicates a pulse wave amplitude PA of the user before the start of the stretch game.

The score data Dl indicates a score in the stretch game. The fluctuation frequency data Dm indicates a respiration frequency of the user. The rising/falling frequency data Dn indicates a frequency of rising and falling of the ceiling T in the stretch game which is calculated, depending on the respiration frequency of the user. The ground angle data Do indicates an inclination angle of the ground B in the stretch game. The limit ground angle data Dp indicates a limit inclination angle of the ground B for the user in the stretch game.

The player character data Dq relates to the player character PC, including inclination data Dq1, flying height data Dq2, situation data Dq3, and position data Dq4. The inclination data Dq1 indicates an inclination angle of the player character PC which is inclined, depending on an inclination of the core unit 70. The flying height data Dq2 indicates a height to which the second player character PC2 is moved up with respect to the first player character PC1. The situation data Dq3 indicates a color or countenance of the player character PC corresponding to a difficulty or easiness level of the user. The position data Dq4 indicates a position in the virtual game world of the player character PC.

The image data Dr includes biological image data Dr1, player character image data Dr2, obstacle image data Dr3, and the like. The biological image data Dr1 is used to display biological information of the user on the monitor 2. The player character image data Dr2 is used to generate a game image of the virtual game world in which the player character PC is arranged. The obstacle image data Dr3 is used to generate a game image of the virtual game world in which an obstacle (the ceiling T and the ground B) is arranged.

Figure 20:
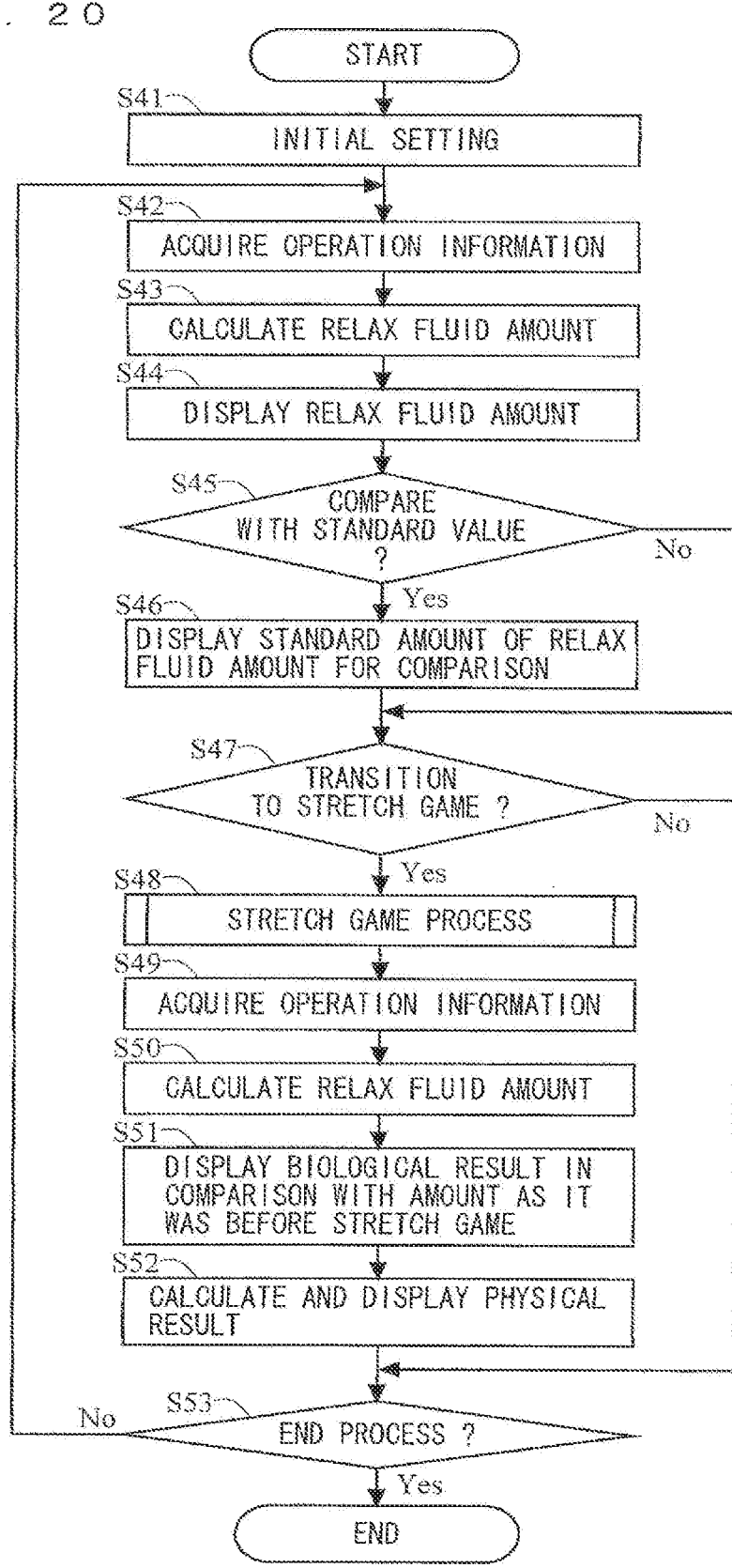
FIG. 20 is a flowchart showing an example of information processing executed in the game apparatus body 5.
Figure 21:
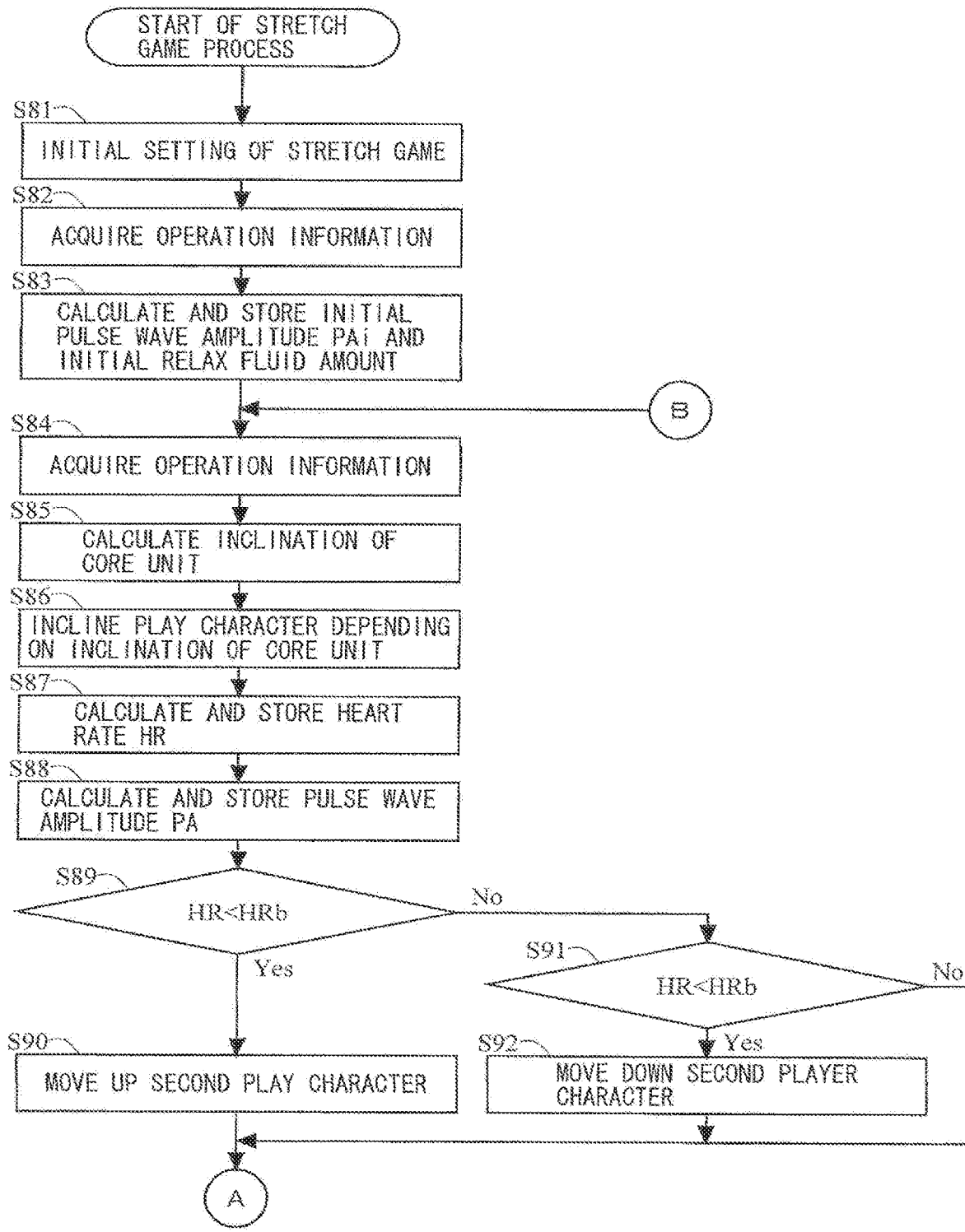
FIG. 21 is a flowchart showing an example of an operation in the first half of a stretch game process in step 48 of FIG. 20.
Figure 22:
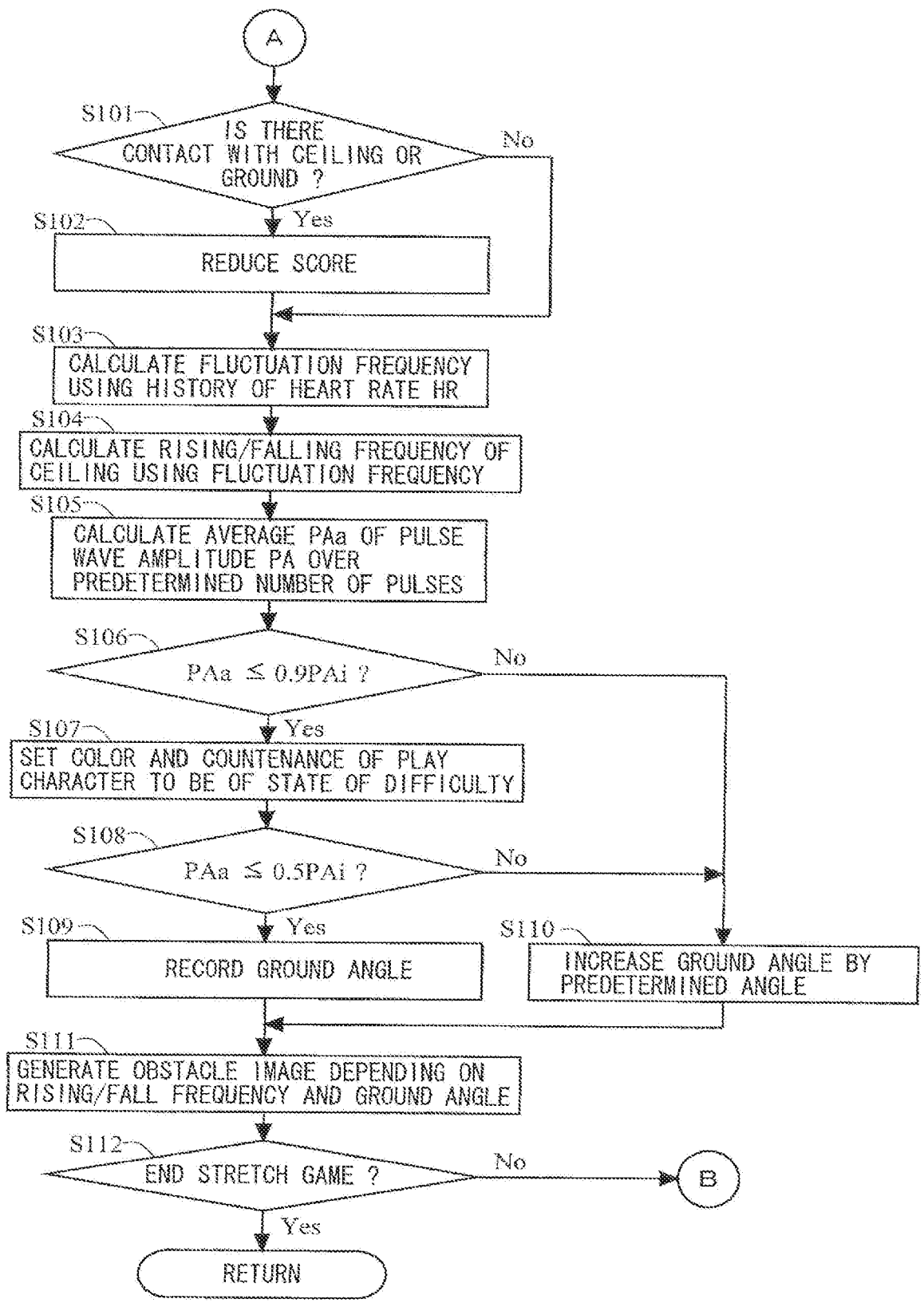
FIG. 22 is a flowchart showing an example of an operation in the second half of the stretch game process in step 48 of FIG. 20.

Next, information processing performed in the game apparatus body 5 will be described in detail with reference to FIGS. 20 to 22. Note that FIG. 20 is a flowchart showing an example of information processing performed in the game apparatus body 5. FIG. 21 is a flowchart showing an example of an operation in the first half of a stretch game process in step 48 of FIG. 20. FIG. 22 is a flowchart showing an example of an operation in the second-half of the stretch game process in step 48 of FIG. 20. Note that, in the flowcharts of FIGS. to 22, of the game processing, processes employing biological information from the vital sensor 76 and an inclination of the core unit 70 will be mainly described, and other game processes which do not directly relate to the present invention will not be described in detail. In FIGS. 20 to 22, each step executed by the CPU 10 is abbreviated to "S".

When the game apparatus body 5 is powered on, the CPU 10 of the game apparatus body 5 executes a boot program stored in the ROM/RTC 13, thereby initializing each unit, such as the main memory or the like. Thereafter, a game program stored on the optical disc 4 is read into the main memory, and execution of the game program is started by the CPU 10. The flowcharts of FIGS. 20 to 22 indicate game processing which is performed after completion of the aforementioned process.

In FIG. 20, the CPU 10 initializes settings for information processing (step 41), and then goes to the next step. For example, in the initialization of settings in step 41, the age of the user, process results until a current time, and the like are initially set. Also, in the initialization of settings in step 41, parameters used in subsequent information processing are each initialized.

Next, the CPU 10 acquires data indicating operation information from the core unit 70 (step 42), and goes to the next step. For example, the CPU 10 acquires operation information received from the core unit 70, and updates the acceleration data Da using an acceleration indicated by the latest acceleration data contained in the operation information. Specifically, the CPU 10 updates the X-axis direction acceleration data Da1 using an acceleration indicated by X-axis direction acceleration data contained in the latest operation information received by the core unit 70. The CPU 10 also updates the Y-axis direction acceleration data Da2 using an acceleration indicated by Y-axis direction acceleration data contained in the latest operation information. The CPU 10 also updates the Z-axis direction acceleration data Da3 using an acceleration indicated by Z-axis direction acceleration data contained in the latest operation information. The CPU 10 also updates the key data Db using an operation performed with respect to the operation sections 72, which is indicated by the latest key data contained in the operation information received from the core unit 70. The CPU 10 also updates the pulse wave data Dc using a pulse wave signal indicated by the latest biological information data contained in the operation information received from the core unit 70.

Next, the CPU 10 calculates a user's relax fluid amount (step 43), and goes to the next step. For example, the CPU 10 calculates a relax fluid amount based on a user's heart rate variance coefficient. Here, the heart rate variance coefficient is calculated using cardiac cycles (R-R intervals; see FIG. 9) over past 100 pulses indicated by a pulse wave signal stored in the pulse wave data Dc. Specifically, the heart rate variance coefficient is calculated by:

heart rate variance coefficient=(the standard deviation of the R-R intervals of 100 pulses/the average of the R-R intervals of 100 pulses)×100

Thereafter, the CPU 10 calculates a relax fluid amount based on the calculated user's heart rate variance coefficient (e.g., a value obtained by multiplying the heart rate variance coefficient by 10 is considered as a relax fluid amount), and updates the relax fluid amount data De using the calculated relax fluid amount.

Next, the CPU 10 generates an image representing biological information in which a current user's relax fluid amount is indicated by a fluid level, and displays the image on the monitor 2 (step 44; see FIG. 10). Thereafter, the CPU 10 determines whether or not to compare the current user's relax fluid amount with a standard amount (step 45). For example, when an operation indicting a command to perform comparison with the standard amount has been performed or when a predetermined period of time has elapsed since displaying of the current user's relax fluid amount on the monitor 2, the CPU 10 decides to compare the current user's relax fluid amount with the standard amount. The CPU 10, when deciding to compare the current user's relax fluid amount with the standard amount, goes to the next step 46. On the other hand, the CPU 10, when not deciding to compare the current user's relax fluid amount with the standard amount, goes to the next step 47.

In step 46, the CPU 10 generates an image which shows the current user's relax fluid amount and the standard amount for comparison, displays the image on the monitor 2 (see FIG. 11), and goes to the next step 47. For example, the CPU acquires a standard value of a relax fluid amount corresponding to the age of the user by referring to the standard value data Df, generates an image showing biological information indicating the standard value as a fluid level, and displays the image on the monitor 2. Here, the standard value may be acquired from the standard value data Df based on the user's age set in step 41, or alternatively, may be acquired from the standard value data Df by the user inputting their age in step 46. Note that, in step 46, a standard value of a relax fluid amount corresponding to the same age as that of the user is acquired, or alternatively, a different standard value may be acquired. For example, a standard value having the same level as that of the current user's relax fluid amount may be acquired. In this case, a standard value of a relax fluid amount corresponding to an age different from the user's age is acquired. However, the user can find out of what age their relax fluid amount corresponds to the level of the standard value.

In step 47, the CPU 10 determines whether or not to go to the stretch game. For example, the CPU 10 presents an option which indicates a game for increasing the user's relax fluid displayed on the monitor 2 (see FIG. 12), and determines whether or not to go to the stretch game, depending on whether or not an operation of selecting the stretch game from the option has been performed. Thereafter, the CPU 10, when going to the stretch game, goes to the next step 48. On the other hand, the CPU 10, when not going to the stretch game, goes to the next step 53.

In step 48, the CPU 10 performs a stretch game process, and goes to the next step. Hereinafter, the stretch game process performed in step 48 will be described with reference to FIGS. 21 and 22.

In FIG. 21, the CPU 10 initializes settings for the stretch game process (step 81), and goes to the next step. For example, in the initialization of settings in step 81, settings for the virtual game world, the player character PC, the ceiling T, the ground B and the like are initialized. Also, in the initialization of settings in step 81, parameters used in subsequent stretch game processes are initialized. For example, the CPU 10 initially sets a score corresponding to a perfect score (e.g., 100 points) into the score data Dl.

Next, the CPU 10 acquires data indicating operation information from the core unit 70 (step 82), and goes to the next step. Note that the process in step 82 is similar to that in step 42 and will not be described in detail.

Next, the CPU 10 calculates the pulse wave amplitude PA and the relax fluid amount before the start of the stretch game of the user, and updates the initial pulse wave amplitude data Dk and the initial relax fluid amount data Dg using the respective calculated values (step 83), and goes to the next step. For example, the CPU 10 refers to a pulse wave signal of the pulse wave data Dc, and calculates a current pulse wave amplitude PA (see FIG. 9) obtained from the pulse wave signal, as an initial pulse wave amplitude PAi. Thereafter, the CPU 10 updates the initial pulse wave amplitude data Dk using the calculated initial pulse wave amplitude PAi. The CPU 10 also refers to a pulse wave signal of the pulse wave data Dc, and calculates a current relax fluid amount based on a heart rate variance coefficient obtained from the pulse wave signal. Thereafter, the CPU 10 updates the initial relax fluid amount data Dg using the calculated relax fluid amount.

Next, the CPU 10 acquires data indicating operation information from the core unit 70 (step 84), and goes to the next step. Note that the process in step 84 is similar to that in step 42 and will not be described in detail.

Next, the CPU 10 calculates an inclination of the core unit 70 with respect to a direction of gravity (step 85), and goes to the next step. For example, the CPU 10 uses an X-axis direction acceleration stored in the X-axis direction acceleration data Da1, a Y-axis direction acceleration stored in the Y-axis direction acceleration data Da2, and a Z-axis direction acceleration stored in the Z-axis direction acceleration data Da3, to calculate an acceleration vector having the acceleration components in the respective directions, and updates the acceleration vector data Dd using the acceleration vector. The CPU 10 also assumes that a direction indicated by the acceleration vector in the acceleration vector data Dd is a direction of a gravitational acceleration acting on the core unit 70. The CPU 10 calculates an inclination of the core unit 70 (an inclination of the controller) with respect to the direction indicated by the acceleration vector, and updates the controller inclination data Dh using the calculated inclination of the core unit 70. Specifically, when the user in an operation attitude as shown in FIG. 13 operates the core unit 70, i.e., when it is assumed that the core unit 70 is operated in a manner which inclines the Z-axis of the core unit 70 around an X-axis direction, an inclination of the Z-axis of the core unit 70 with respect to a direction of the gravitational acceleration is calculated as the inclination of the core unit 70 (the inclination of the controller).

Next, the CPU 10 inclines the player character PC with respect to the virtual game world, depending on the inclination of the core unit 70, displays the inclined player character PC on the monitor 2 (step 86), and goes to the next step. For example, when it is assumed that the core unit 70 is operated in a manner which inclines the Z-axis of the core unit 70 around the X-axis direction of the core unit 70, then if the user inclines the core unit 70 so that its Z-axis is inclined to the right (as the user faces the monitor 2) at an angle of α, the CPU 10 calculates an inclination angle which inclines the player character PC to the right (as the user faces the monitor 2) at an angle of α in the virtual game world in synchronization with the act of inclining, and updates the inclination data Dq1 using the calculated inclination angle. Thereafter, the CPU 10 inclines the player character PC in the virtual game world, depending on the inclination angle indicated by the inclination data Dq1, and displays the inclined player character PC on the monitor 2 (see FIGS. 16 and 17).

Next, the CPU 10 calculates a heart rate HR of the user, updates a history of the heart rate data Di using the calculated heart rate HR (step 87), and goes to the next step. For example, the CPU 10 refers to a pulse wave signal of the pulse wave data Dc, and calculates a current cardiac cycle (R-R interval; see FIG. 9). Thereafter, the CPU 10 calculates a heart rate HR by dividing 60 sec by the cardiac cycle, and updates the history of heart rates HR by adding data indicating the newly calculated heart rate HR to the heart rate data Di. Note that, as will be seen from a description below, if the history of heart rates HR is stored in an amount corresponding to a predetermined period of time, a process can be performed, and therefore, when a new heart rate HR is added, a past heart rate HR exceeding the time period may be erased.

Next, the CPU 10 calculates a pulse wave amplitude PA of the user, updates a history of the pulse wave amplitude data Dj using the calculated pulse wave amplitude PA (step 88), and goes to the next step. For example, the CPU 10 refers to a pulse wave signal of the pulse wave data Dc, and calculates a current pulse wave amplitude PA (see FIG. 9) obtained from the pulse wave signal. Thereafter, the CPU 10 adds data indicating the newly calculated pulse wave amplitude PA to the pulse wave amplitude data Dj to update the history of pulse wave amplitudes PA. Note that, as will be seen from a description below, if the history of pulse wave amplitudes PA is stored in an amount corresponding to a predetermined period of time, a process can be performed, and therefore, when a new pulse wave amplitude PA is added, a past pulse wave amplitude PA exceeding the time period may be erased.

Next, the CPU 10 determines whether or not the heart rate HR calculated in step 87 is smaller than the previously calculated heart rate HRb (step 89), and determines whether or not the heart rate HR calculated in step 87 is larger than the previously calculated heart rate HRb (step 91). Thereafter, the CPU 10, when the heart rate HR calculated in step 87 is smaller than the previously calculated heart rate HRb (Yes in step 89), goes to the next step 90. Also, the CPU 10, when the heart rate HR calculated in step 87 is larger than the previously calculated heart rate HRb (Yes in step 91), goes to the next step 92. On the other hand, the CPU 10, when the heart rate HR calculated in step 87 is the same as the previously calculated heart rate HRb (No in both steps 89 and 91), goes to the next step 101 (see FIG. 22).

In step 90, the CPU 10 moves up the second player character PC2 with respect to the first player character PC1 by a predetermined amount in the virtual game world, displays the second player character PC2 thus moved up on the monitor 2, and goes to the next step 101 (see FIG. 22). For example, the CPU 10 calculates a flying height of the second player character PC2 which is obtained by increasing the distance between the first player character PC1 and the second player character PC2 in the virtual game world by a predetermined length, and updates the flying height data Dq2 using the flying height. Thereafter, the CPU 10 moves up the second player character PC2 with respect to the first player character PC1 in the virtual game world so that they are separated by the flying height indicated by the flying height data Dq2, and displays the second player character PC2 thus moved up on the monitor 2 (see FIG. 15). Note that the distance between the first player character PC1 and the second player character PC2 which are separated in step 90 may be increased by a constant amount, or an amount which varies depending on a difference between the heart rate HRb and the heart rate HR.

On the other hand, in step 91, the CPU 10 moves down the second player character PC2 with respect to the first player character PC1 by a predetermined amount in the virtual game world, displays the second player character PC2 thus moved down on the monitor 2, and goes to the next step 101 (see FIG. 22). For example, the CPU 10 calculates a flying height of the second player character PC2 which is obtained by decreasing the distance between the first player character PC1 and the second player character PC2 in the virtual game world by a predetermined length, and updates the flying height data Dq2 using the flying height. Thereafter, the CPU 10 moves up the second player character PC2 with respect to the first player character PC1 so that they are separated by the flying height indicated by the flying height data Dq2 in the virtual game world, and displays the second player character PC2 thus moved up on the monitor 2. Note that an amount by which the second player character PC2 is moved down with respect to the first player character PC1 in the virtual game world, is decided to a value which prevents the second player character PC2 from overlapping the first player character PC1. In other words, the second player character PC2 is not moved down to a position which causes the second player character PC2 to overlap the first player character PC1 in the virtual game world. Note that the distance between the first player character PC1 and the second player character PC2 which is reduced in step 91 may be decreased by a predetermined amount, or an amount which varies depending on a difference between the heart rate HRb and the heart rate HR.

Referring to FIG. 22, in step 101, the CPU 10 determines whether or not the player character PC contacts the ceiling T or the ground B in the virtual game world. For example, when the player character PC is flying, then if the first player character PC1 contacts the ground B or the second player character PC2 contacts the ceiling T, the CPU 10 determines that the player character PC contacts the ceiling T or the ground B. Thereafter, the CPU 10, when the player character PC contacts the ceiling T or the ground B, goes to the next step 102. On the other hand, if the player character PC contacts neither of the ceiling T and the ground B, the CPU 10 goes to the next step 103.

In step 102, the CPU 10 reduces the score of the stretch game by a predetermined number of points, and goes to the next step 103. For example, the CPU 10 subtracts a point or points corresponding to a contact with the ceiling T or the ground B from the score indicated by the score data Dl, and updates the score data Dl using the resultant score. Here, the number of subtracted points may be changed, depending on a situation that the player character PC contacts the ceiling T or the ground B. As a first example, the number of subtracted points is increased with a period of time during which the player character PC contacts the ceiling T or the ground B. As a second example, the number of subtracted points is increased with an area on which the player character PC overlaps the ceiling T or the ground B. As a third example, the number of subtracted points is increased with the number of times at which the player character PC contacts the ceiling T or the ground B. As a fourth example, the number of subtracted points is changed, depending on which of the ceiling T and the ground B the player character PC contacts. As a fifth example, the number of subtracted points is changed in accordance with a combination of at least two of the first to fourth examples.

Note that, in the aforementioned process, when the player character PC contacts or overlaps the ceiling T or the ground B, the score of the stretch game is reduced to degrade the assessment. Therefore, the lower the score of the stretch game, the poorer the assessment. Alternatively, the score may be changed in other fashions. As a first example, the score of the stretch game at the start is set to 0 points, and when the player character PC contacts or overlaps the ceiling T or the ground B, the score of the stretch game is increased to degrade the assessment. In this case, the higher the score of the stretch game, the poorer the assessment. As a second example, the score of the stretch game at the start is set to 0, and is incremented with time in the stretch game, and when the player character PC contacts or overlaps the ceiling T or the ground B in the stretch game, the increment is canceled to degrade the assessment. In this case, the lower the score of the stretch game, the poorer the assessment.

In step 103, the CPU 10 uses a history of heart rates HR to calculate a frequency (fluctuation frequency) at which the heart rate HR rises and falls, and goes to the next step. For example, the CPU 10 acquires a history of user's heart rates HR until a current time by referring to the heart rate data Di. Thereafter, the CPU 10 calculates the fluctuation frequency of heart rates HR from the history of heart rates HR, and updates the fluctuation frequency data Dm using the calculated fluctuation frequency. Here, if the heart rate HR calculated in this embodiment is increasing, it is determined that the user is inhaling, and if the heart rate HR is decreasing, it is determined that the user is exhaling. In other words, the fluctuation frequency corresponds to a frequency (respiration frequency) at which the user breathes.

Next, the CPU 10 uses the fluctuation frequency calculated in step 103 to calculate a frequency (rising/falling frequency) at which the ceiling T is caused to rise and fall (step 104), and goes to the next step. For example, the CPU 10 calculates a frequency obtained by slowing a fluctuation frequency indicated by the fluctuation frequency data Dm to a predetermined fraction thereof (e.g., 80% of the fluctuation frequency) as the rising/falling frequency, and updates the rising/falling frequency data Dn using the calculated rising/falling frequency.

Next, the CPU 10 calculates an average value PAa of pulse wave amplitudes PA over a predetermined number of pulses (step 105). Thereafter, the CPU 10 determines whether or not the calculated average value PAa is 90% or less of the initial pulse wave amplitude PAi (step 106). When PAa≤0.9PAi, the CPU goes to the next step 107. On the other hand, when 0.9PAi<PAa, the CPU 10 goes to the next step 110.

In step 107, the CPU 10 sets a color or countenance of the player character PC displayed in the virtual game world, which represents a level of difficulty, as the situation data Dq3, displays the player character PC in a state corresponding to the difficulty level on the monitor 2, and goes to the next step. Here, step 107 is executed in a state that the pulse wave amplitude PA of the user is reduced to 90% or less of that at the start of the stretch game, i.e., it can be determined that "the user has difficulty." In the stretch game, when it can be determined that the user has difficulty, the CPU 10 changes the color or countenance of the player character PC, depending on the level of difficulty or easiness of the user (see FIG. 17).

In step 108, the CPU 10 determines whether or not the calculated average value PAa is 50% or less of the initial pulse wave amplitude PAi. When PAa>0.5PAi, the CPU 10 goes to the next step 110. When PAa≤0.5PAi, the CPU 10 goes to the next step 109.

In step 109, the CPU 10 records the current inclination angle of the ground B as a limit inclination angle, and goes to the next step 111. Here, step 109 is executed is in a state in which the pulse wave amplitude PA of the user is 50% or less of that at the start of the stretch game, i.e., it can be determined that "the user has much difficulty." In the stretch game, when it can be determined that the user has much difficulty, the CPU 10 determines that the current inclination angle of the ground B is a limit for the user, and updates the limit ground angle data Dp using the inclination angle.

On the other hand, in step 110, the CPU 10 increases the inclination angle of the ground B by a predetermined angle, and goes to the next step 111. For example, the CPU 10 adds a predetermined angle to an inclination angle indicated by the ground angle data Do to calculate a new inclination angle, and updates the ground angle data Do using the calculated inclination angle.

In step 111, the CPU 10 generates the ceiling T and the ground B (obstacle images) based on a rising/falling frequency indicated by the rising/falling frequency data Dn and an inclination angle indicated by the ground angle data Do, displays the ceiling T and the ground B on the monitor 2, and goes to the next step. For example, the CPU 10 displays the ceiling T which is scrolled while adjusting a shape of the ceiling T so that the ceiling T rises and falls at a rising/falling frequency indicated by the rising/falling frequency data Dn, when the player character PC flies in the virtual game world. The CPU 10 also displays on the monitor the ground B which is inclined at an inclination angle indicated by the ground angle data Do in the virtual game world.

Next, the CPU 10 determines whether or not to end the stretch game (step 112). For example, the stretch game is ended under conditions that conditions under which the game is over are satisfied, that the user performs an operation of ending the stretch game, or the like. The CPU 10, when not ending the stretch game, returns to step 84 (see FIG. 21) and repeats the process thereof, and when ending the stretch game, ends the subroutine process.

Referring back to FIG. 20, after the stretch game process of step 48, the CPU 10 acquires data indicating operation information from the core unit 70 (step 49), and goes to the next step. Note that the process in step 49 is similar to that in step 42 and will not be described in detail.

Next, the CPU 10 calculates a relax fluid amount of the user after the stretch game (step 50), and goes to the next step. Note that the process in step 50 is similar to that in step 43 and will not be described in detail.

Next, the CPU 10 generates an image representing biological information which indicates a current user's relax fluid amount (after the stretch game) and a user's relax fluid amount before the start of the stretch game as respective fluid levels, displays the image on the monitor 2 (step 51; see FIG. 18), and goes to the next step. For example, the CPU 10 generates a biological information image indicating heights of fluid levels which represent a relax fluid amount indicated by the relax fluid amount data De as a current user's relax fluid amount and a relax fluid amount indicated by the initial relax fluid amount data Dg as a user's relax fluid amount before the start of the stretch game. The CPU 10 also compares the current user's relax fluid amount with the relax fluid amount before the start of the stretch game to calculate an increase or a decrease in user's relax fluid amount. Thereafter, the CPU 10 displays the biological information image and an image indicating the increase or decrease on the monitor 2. As a result, the user can find out how their relax fluid amount has been changed by performing the stretch game.

Next, the CPU 10 calculates a user's physical result of the stretch game, displays the physical result on the monitor 2 (step 52), and goes to the next step. For example, the CPU 10 uses the result of the stretch game to calculate the pliancy of the user's body as a physical result. Specifically, the CPU 10 displays the pliancy (pliancy score) of the user using a limit inclination angle indicated by the limit ground angle data Dp. As an example, the CPU 10 compares the user's limit inclination angle with an ideal inclination angle in the stretch game, calculates a user's pliancy (pliancy score) based on a difference therebetween, and displays the user's pliancy.

Next, the CPU 10 determines whether or not to end the process (step 53). For example, the process is ended under conditions that conditions under which the game is over are satisfied, that the user performs an operation of ending the stretch game, or the like. The CPU 10, when not ending the process, returns to step 42 and repeats the process thereof, and when ending the process, ends the process of the flowchart.

Thus, according to the aforementioned information process, predetermined presentation is performed using not only a current user's biological signal, but also a current user's motion or attitude. Therefore, the user can recognize a state of their body to further extent, and promote a change in body state by utilizing a motion or an attitude of the user in combination. For example, in the stretch game, an obstacle image (the ceiling T) is generated based on a user's biological signal (respiration frequency obtained from a pulse wave signal). Also, in the stretch game, the second player character PC2 is moved up and down based on a user's biological signal (the act of inhaling/exhaling obtained from a pulse wave signal). Moreover, in the stretch game, a color or countenance of the player character PC is changed and an inclination angle of an obstacle image (the ground B) is controlled based on a user's biological signal (the level of difficulty or easiness of the user obtained from a pulse wave signal). On the other hand, in the stretch game, the player character PC is inclined based on a current user's motion or attitude (an attitude of the core unit 70).

Note that, in the stretch game, an obstacle image (the ceiling T and the ground B) is used to instruct the user to take a predetermined motion or attitude. Here, rising and falling of the ceiling T and an inclination angle of the ground B are controlled based on a user's biological signal. Alternatively, they may be controlled irrespective of a user's biological signal. For example, the ceiling T may be controlled at a predetermined rising/falling frequency, and an inclination angle of the ground B may be controlled to gradually increase to a predetermined angle, whereby rising and falling of the ceiling T and an inclination angle of the ground B can be controlled irrespective of a user's biological signal. In this case, although the user is instructed to take a predetermined motion or attitude irrespective of a user's biological signal or information obtained from the core unit 70, the player character PC (upward and downward movements, inclinations, a color or countenance, etc.) is controlled based on both a user's biological signal and a current user's motion or attitude (an inclination of the core unit 70). Note that, when the present invention is applied to other games, various ways of instruction and control may be contemplated.

Note that, in the description above, predetermined presentation is performed using parameters, such as a heart rate variance coefficient, a relax fluid amount, a cardiac cycle (R-R interval), a heart rate HR, a respiration frequency, a pulse wave amplitude PA, a difficulty or easiness level, and the like, which are obtained from a user's biological signal (pulse wave signal). Alternatively, other parameters obtained from a user's biological signal (pulse wave signal) may be used. As a first example, predetermined presentation may be performed using a blood flow rate obtained from a user's biological signal (pulse wave signal). For example, the blood flow rate can be obtained by dividing a pulse wave area PWA (see FIG. 9) obtained from a pulse wave signal by a heart rate HR. As a second example, predetermined presentation may be performed using a user's tension or liveliness level (an activity level of the sympathetic nervous system) obtained from a biological signal (pulse wave signal). For example, a heart rate HR of the user at rest is compared with a current heart rate HR to calculate a user's tension or liveliness level (e.g., (current heart rate HR/heart rate HR at rest)×100).

Also, in the description above, a portion (e.g., a fingertip) of the user's body is irradiated with infrared light, and a user's biological signal (pulse wave signal) is obtained based on the amount of infrared light which is transmitted through the body portion and is sensed, i.e., a change in volume of a blood vessel is detected by a so-called optical method to obtain a volume pulse wave. Alternatively, in the present invention, a user's biological signal may be acquired using sensors of other types which obtain physiological information which occurs when the user performs a physical activity. For example, a user's biological signal may be acquired by detecting a change in pressure in a blood vessel due to pulsation of the arterial system to obtain a pressure pulse wave (e.g., a piezoelectric method). Alternatively, a muscle potential or a heart potential of the user may be acquired as user's biological information. The muscle or heart potential can be detected by a commonly used method employing electrodes. For example, a user's biological signal can be acquired based on, for example, a minute change in current in the user's body. Alternatively, a blood flow of the user may be acquired as user's biological information. A blood flow is measured as a pulsating blood flow per heart pulse using an electromagnetic method, an ultrasonic method or the like, thereby making it possible to acquire the pulsating blood flow as a user's biological signal. A vital sensor may be attached to a portion (e.g., a chest, an arm, an ear lobe, etc.) other than a finger portion of the user so as to obtain various biological signals described above. Strictly speaking, there may be a difference between pulsation and heartbeat, depending on the acquired biological signal. However, a heart rate and a pulse rate are considered to be substantially equal to each other, and therefore, the acquired biological signal can be processed in a manner similar to that of the aforementioned process.

Also, in the description above, the vital sensor 76 transmits data indicating a pulse wave signal to the game apparatus body 5, which in turn calculates various parameters from the pulse wave signal. Alternatively, data in other process steps may be transmitted to the game apparatus body 5. For example, the vital sensor 76 may calculate a parameter, such as a heart rate variance coefficient, a relax fluid amount (an activity level of the parasympathetic nervous system), a cardiac cycle (R-R interval), a heart rate HR, a respiration frequency, a pulse wave amplitude PA, an activity level of the sympathetic nervous system, a difficulty or easiness level or the like, and transmit data indicating the parameter to the game apparatus body 5. Alternatively, data halfway through calculation of the parameter from a pulse wave signal may be transmitted from the vital sensor 76 to the game apparatus body 5.

Also, in the description above, a current user's motion or attitude (a motion of the core unit 70) is detected using an acceleration indicated by triaxial acceleration data obtained from the acceleration sensor 701. Alternatively, a current user's motion or attitude may be detected using data outputted from sensors of other types fixed to the core unit 70. For example, it is possible to use data outputted from a sensor (an acceleration sensor, an inclination sensor) which outputs data corresponding to an inclination of the core unit 70 with respect to a direction of gravity (hereinafter simply referred to as an "inclination"), a sensor (a magnetic sensor) which outputs data corresponding to an orientation of the core unit 70, a sensor (a gyro-sensor) which outputs data corresponding to a rotational movement of the core unit 70, or the like. The acceleration sensor and the gyro-sensor may be either one which can detect accelerations along multiple axes or one which can detect an acceleration along only a single axis. Alternatively, these sensors may be combined to perform more accurate detection. Note that a camera (e.g., the imaging information calculation section 74) fixed to the core unit 70 can be used as the sensor. In this case, an image captured by the camera varies, depending on a motion of the core unit 70, and therefore, the motion of the core unit 70 can be determined by analyzing the image.

The sensor may be provided outside the core unit 70, depending on the type thereof. As an example, a camera as the sensor is used to shoot the whole core unit 70 outside the core unit 70, and an image of the core unit 70 included in the captured image is analyzed, thereby making it possible to determine a motion of the core unit 70. Moreover, a system including a unit fixed to the core unit 70 and another unit provided outside the core unit 70, which cooperate with each other, may be used. As an example, a light source unit is provided outside the core unit 70, and a camera fixed to the core unit 70 is used to capture light from the light source unit. By analyzing an image captured by the camera, a motion of the core unit 70 can be determined. As another example, a system including a magnetic field generator provided outside the core unit 70 and a magnetic sensor fixed to the core unit 70, or the like, may be used.

When the sensor can be provided outside the core unit 70, the core unit 70 may not be used. As an example, a camera as the sensor is used to simply shoot the user, and an image of the user included in the captured image is analyzed, thereby making it possible to determine a user's motion or attitude. Alternatively, a sensor which is provided in an input device which is operated by the user standing thereon (e.g., a board controller), and senses a weight acting on the input device or the presence or absence of an object, can be used to determine a motion or an attitude of the user operating the input device. If sensors of these embodiments are used to determine a user's motion or attitude, the core unit 70 may not be used.

Also, in the description above, a motion of the player character PC, a displayed state of the player character PC, or an obstacle image is changed, depending on a current user's biological signal and a current user's motion or attitude, thereby presenting an image indicating a current user's state, an instruction image for prompting the user to change their state, or the like. Alternatively, presentation to the user may be performed in other fashions. For example, information indicating a current user's motion or attitude, an instruction for prompting the user to change their state, or the like may be presented using audio, light or the like, depending on a current user's biological signal and a current user's motion or attitude. For example, audio can be emitted via the loudspeakers 2a or the loudspeaker 706 in the game system 1. Specifically, a frequency at which the user should breathe may be indicated by alternately repeating speech sounds "inhale" and "exhale" instead of presenting the ceiling T which rises and falls. Also, an instruction for the user to act may be provided by repeatedly emitting a speech sound "incline a little more" until a limit inclination angle is reached, and emitting a speech sound "stop now" when the limit inclination angle is reached, instead of presenting the ground B which is inclined.

Also, in the description above, a game is used in which the player character PC is moved in a two-dimensional virtual game world, depending on a user's pulse wave signal and an inclination of the core unit 70. The present invention is applicable to a game in which the player character PC is moved in a three-dimensional virtual game space, and the way in which the player character PC is displayed is changed.

Also, in the examples above, the present invention is applied to the stationary game apparatus 3. The present invention is also applicable to any apparatus that includes at least a vital sensor, a sensor (e.g., an acceleration sensor, an inclination sensor, etc.) for detecting a user's motion or attitude, and an information processing device for executing a process, depending on information obtained from these sensors. For example, the present invention is also applicable to general devices, such as a personal computer, a mobile telephone, a Personal Digital Assistant (PDA), a hand-held game apparatus, and the like.

Also, in the description above, the core unit 70 and the game apparatus body 5 are connected by wireless communication. Alternatively, the core unit 70 and the game apparatus body 5 may be electrically connected via a cable. In this case, a cable connected to the core unit 70 is connected to a connection terminal of the game apparatus body 5.

Also, of the core unit 70 and the vital sensor 76 constituting the controller 7, the communication section 75 is provided only in the core unit 70. Alternatively, a communication section which wirelessly transmits biological information data to the game apparatus body 5 may be provided in the vital sensor 76. Alternatively, the communication section may be provided in each of the core unit 70 and the vital sensor 76. For example, the communication sections provided in the core unit 70 and the vital sensor 76 may each wirelessly transmit biological information data or operation data to the game apparatus body 5. Alternatively, the communication section of the vital sensor 76 may wirelessly transmit biological information data to the core unit 70, and the communication section 75 of the core unit 70 may receive it and thereafter may wirelessly transmit operation data of the core unit 70 along with the biological information data of the vital sensor 76 to the game apparatus body 5. In these cases, the connection cable 79 for electrically connecting the core unit 70 and the vital sensor 76 is no longer required.

Also, the shape of the core unit 70 and the shapes, number, arrangement and the like of the operation sections 72 thereon, which are described above, are only for illustrative purposes. Even in the case of other shapes, numbers, arrangements and the like, the present invention can be achieved. Also, the shape of the vital sensor 76 and the types, number, arrangement and the like of the components therein, which are described above, are only for illustrative purposes. Even in the case of other types, numbers, arrangements and the like, the present invention can be achieved. Also, the aforementioned coefficients, criteria, expressions, procedures and the like used in the processes are only for illustrative purposes. Even in the case of other values, expressions and procedures, the present invention can be achieved.

Also, the game program of the present invention may be supplied to the game apparatus body 5 not only from an external storage medium, such as the optical disc 4 or the like, but also via a wireless or wired communication line. Alternatively, the game program may be previously stored on a non-volatile storage device of the game apparatus body 5. Examples of the information storage medium storing the game program includes a CD-ROM, a DVD, an optical disc-like storage device similar to those, and a non-volatile semiconductor memory.

The storage medium having stored thereon the information processing program and the information processing device according to the present invention are capable of prompting the user to change their state by performing predetermined presentation using a current user's biological signal and a current user's motion or attitude. Therefore, the present invention is useful as an information processing program, an information processing device and the like which manage user's biological information or the like, and a game program, a game apparatus and the like which perform game processing using user's biological information or user's operation information.

While the invention has been described in detail, the foregoing description is in all aspects illustrative and not restrictive. It is to be understood that numerous other modifications and variations can be devised without departing from the scope of the invention. It is also to be understood that the scope of the invention is indicated by the appended claims rather than by the foregoing description. It is also to be understood that the detailed description herein enables one skilled in the art to make changes coming within the meaning and equivalency range of the present invention. It is also to be understood that all of the patents, patent applications and publications recited herein are hereby incorporated by reference as if set forth in their entirety herein.

It should be understood throughout the present specification that expression of a singular form includes the concept of their plurality unless otherwise mentioned. Specifically, articles or adjectives for a singular form (e.g., "a", "an", "the", etc. in English) include the concept of their plurality unless otherwise mentioned. It should be also understood that the terms as used herein have definitions typically used in the art unless otherwise mentioned. Thus, unless otherwise defined, all scientific and technical terms have the same meanings as those generally used by those skilled in the art to which the present invention pertain. If there is contradiction, the present specification (including the definitions) precedes.

What is claimed is:

1. A game system comprising:
    a controller comprising:
        a physiological sensor for generating physiological data associated with a user;
        an input device;
        an inertial sensor for generating inertial sensor data indicative of activity of the user;
        memory for storing the inertial sensor data and the physiological data; and
        communication circuitry for communicating the physiological data and the inertial sensor data; and
    a game apparatus comprising:
        communication circuitry for receiving the inertial sensor data and the physiological data communicated by the controller; and
        processing circuitry configured to generate image data for a game, the generated image data including first image data for a first object controlled based on one or more of the received inertial sensor data and the physiological data, and second image data, different from the first image data, for score or numerical value information based on control of the first object,
    wherein the processing circuitry is further configured to generate third image data for a second object and the score or numerical value information is based on a positional relationship between the first object and the second object.

2. The game system according to claim 1, wherein the physiological sensor comprises an electrode.

3. The game system according to claim 1, wherein the physiological sensor is configured to generate physiological data associated with heart rate.

4. The game system according to claim 1, wherein the inertial sensor comprises a triaxial accelerometer.

5. The game system according to claim 1, wherein the game apparatus further comprises memory and the processing circuitry is configured to store the received physiological data in the memory as a history.

6. The game system according to claim 1, wherein the first object comprises an animated character corresponding to the user.

7. The game system according to claim 1, wherein the controller further comprises a vibrator.

8. The game system according to claim 1, wherein the input device comprises an operation button.

9. The game system according to claim 1, wherein aspects of movement of the first object are controlled based on the one or more of the received inertial sensor data and the physiological data.

10. The game system according to claim 1, wherein the second object is controlled based on the physiological data.

11. The game system according to claim 1, wherein the score or numerical value information comprises a score that is reduced based on contact between the first object and the second object.

12. The game system according to claim 1, wherein the first object is controlled based on both the received inertial sensor data and the received physiological data.

13. A method comprising:
    receiving, from a controller, inertial sensor data indicative of activity of a user and physiological data associated with the user; and
    generating image data for a game, the generated image data including first image data for a first object controlled based on one or more of the received inertial sensor data and the physiological data, and second image data, different from the first image data, for score or numerical value information based on control of the first object, wherein the method further comprises generating third image data for a second object, and wherein the score or numerical value information is based on a positional relationship between the first object and the second object.

14. The method according to claim 13, wherein the second object is controlled based on the physiological data.

15. The method according to claim 13, wherein the score or numerical value information comprises a score that is reduced based on contact between the first object and the second object.

16. A non-transitory computer-readable medium storing a game program which, when executed by processing circuitry of a game apparatus, causes the game apparatus to perform operations comprising:

receiving, from a controller, inertial sensor data indicative of activity of a user and physiological data associated with the user; and generating image data for a game, the generated image data including first image data for a first object controlled based on one or more of the received inertial sensor data and the physiological data, and second image data, different from the first image data, for score or numerical value information based on control of the first object, wherein the operations further comprise generating third image data for a second object, and wherein the score or numerical value information is based on a positional relationship between the first object and the second object.

17. A game system comprising the non-transitory computer-readable medium according to claim 16.

18. The game system according to claim 17, further comprising a controller comprising a physiological sensor for generating the physiological data and an inertial sensor for generating the inertial sensor data.

19. The non-transitory computer-readable medium according to claim 16, wherein the second object is controlled based on the physiological data.

20. The non-transitory computer-readable medium according to claim 16, wherein the score or numerical value information comprises a score that is reduced based on contact between the first object and the second object.

21. A controller comprising:
- a physiological sensor for generating physiological data associated with a user;
- an input device;
- an inertial sensor for generating inertial sensor data indicative of activity of the user;
- memory for storing the inertial sensor data and the physiological data; and
- communication circuitry for communicating the physiological data and the inertial sensor data to a game apparatus for use in generating image data including first image data for a first object controlled based on one or more of the inertial sensor data and the physiological data, and second image data, different from the first image data, for score or numerical information based on control of the first object, wherein the image data includes third image data for a second object and the score or numerical value information is based on a positional relationship between the first object and the second object.

22. A game system comprising the controller according to claim 21.

23. The controller according to claim 21, wherein the second object is controlled based on the physiological data.

24. The controller according to claim 21, wherein the score or numerical value information comprises a score that is reduced based on contact between the first object and the second object.

* * * * *